(12) United States Patent
Takemoto et al.

(10) Patent No.: US 10,653,350 B2
(45) Date of Patent: May 19, 2020

(54) DATA PROCESSING DEVICE, MONITORING SYSTEM, AWAKENING SYSTEM, DATA PROCESSING METHOD, AND DATA PROCESSING PROGRAM

(71) Applicant: OMRON Corporation, Kyoto-shi, Kyoto (JP)

(72) Inventors: Ayumi Takemoto, Kyoto (JP); Koichi Kinoshita, Kyoto (JP); Hitoshi Mukai, Kyoto (JP); Shigenori Nagae, Kyoto (JP); Yamato Takeuchi, Kyoto (JP)

(73) Assignee: OMRON Corporation, Kyoto-shi (JP)

( * ) Notice: Subject to any disclaimer, the term of this patent is extended or adjusted under 35 U.S.C. 154(b) by 0 days.

(21) Appl. No.: 16/381,101

(22) Filed: Apr. 11, 2019

(65) Prior Publication Data
US 2019/0336059 A1 Nov. 7, 2019

(30) Foreign Application Priority Data
May 7, 2018 (JP) .................................. 2018-089368

(51) Int. Cl.
*G08B 21/06* (2006.01)
*A61B 5/18* (2006.01)
(Continued)

(52) U.S. Cl.
CPC .............. *A61B 5/18* (2013.01); *A61B 5/0077* (2013.01); *A61B 5/1114* (2013.01); *A61B 5/163* (2017.08);
(Continued)

(58) Field of Classification Search
CPC .......... G06F 3/012; G06F 3/013; G06F 1/163; G06F 3/017; H04N 5/23203; H04W 4/80;
(Continued)

(56) References Cited

U.S. PATENT DOCUMENTS 9,290,174 B1* 3/2016 Zagorski ................ B60K 28/06
2007/0217683 A1 9/2007 Kinoshita
(Continued)

FOREIGN PATENT DOCUMENTS

| JP | 2007-249280 A | 9/2007 |
|----|---------------|--------|
| JP | 5255063 B2 | 8/2013 |
| WO | 2006/051607 A1 | 5/2006 |

*Primary Examiner* — Daniel Previl
(74) *Attorney, Agent, or Firm* — Metrolex IP Law Group, PLLC

(57) ABSTRACT

A data processing device that performs data processing of monitoring a person, the data processing device includes: a calculator configured to calculate pupil movement and head movement of the person; an evaluator configured to evaluate a suitability degree of a situation in calculating the VOR; a provision unit configured to provide the suitability degree evaluated by the evaluator to data calculated by the calculator; a selector configured to select a first technique of calculating the sleepiness based on the VOR of the person or a second technique different from the first technique based on the suitability degree provided to the data; a first sleepiness calculator configured to calculate the sleepiness based on the first technique when the selector selects the first technique; and a second sleepiness calculator configured to calculate the sleepiness based on the second technique when the selector selects the second technique.

20 Claims, 5 Drawing Sheets

(51) Int. Cl.
*A61B 5/00* (2006.01)
*A61B 5/16* (2006.01)
*A61B 5/11* (2006.01)

(52) U.S. Cl.
CPC ............ *A61B 5/4809* (2013.01); *A61B 5/742* (2013.01); *A61B 5/7405* (2013.01); *A61B 5/746* (2013.01); *A61B 5/7455* (2013.01); *G08B 21/06* (2013.01)

(58) Field of Classification Search
CPC ..... A61B 5/0077; A61B 5/1114; A61B 5/163; A61B 5/18; A61B 5/4809; A61B 5/7405; A61B 5/742; A61B 5/7455; A61B 5/746; B60W 40/08; B60W 2040/0827; B60W 2040/0872; B60W 2540/00; B60W 50/14; B60W 50/16; G08B 21/06; B60K 2370/149; B60K 28/066; G06K 9/00617; G06K 9/00845; G06N 20/00; G06Q 40/08; H04L 67/12

USPC ............ 340/575, 576, 582, 602, 669, 691.6, 340/825.19, 825.36, 825.49, 384.3
See application file for complete search history.

(56) References Cited

U.S. PATENT DOCUMENTS

| | | | |
|---|---|---|---|
| 2008/0130961 A1 | 6/2008 | Kinoshita | |
| 2008/0231461 A1* | 9/2008 | Sanchez | B60K 28/066 340/575 |
| 2010/0049066 A1* | 2/2010 | Hatakeyama | A61B 5/04012 600/509 |
| 2012/0069301 A1* | 3/2012 | Hirata | A61B 3/112 351/209 |
| 2013/0307686 A1* | 11/2013 | Frauenthal | A61B 5/746 340/539.12 |
| 2017/0312614 A1* | 11/2017 | Tran | H04W 4/027 |
| 2018/0072327 A1* | 3/2018 | Seppelt | G06Q 40/08 |

* cited by examiner

DATA PROCESSING DEVICE, MONITORING SYSTEM, AWAKENING SYSTEM, DATA PROCESSING METHOD, AND DATA PROCESSING PROGRAM

CROSS-REFERENCE TO RELATED APPLICATION

This application is based on Japanese Patent Application No. 2018-089368 filed with the Japan Patent Office on May 7, 2018, the entire contents of which are incorporated herein by reference.

FIELD

The disclosure relates to a data processing device, a monitoring system, an awakening system, a data processing method, and a data processing program.

BACKGROUND

Japanese Patent No. 5255063 discloses a sleepiness sign detection device aiming at detecting a sign before a driver of a vehicle feels sleepiness using vestibulo-ocular reflex induced by a head movement.

The sleepiness sign detection device of Japanese Patent No. 5255063 includes a head movement detection unit for detecting head movement, an eye movement detection unit for detecting eye movement, an ideal eye movement angular velocity calculation unit for calculating ideal eye movement angular velocity based on head movement data detected by the head movement detection unit, an eye rotation angular velocity calculation unit for calculating eye rotation angular velocity based on eye movement data detected by the eye movement detection unit, and a sleepiness sign determination unit for detecting Vestibulo-Ocular Reflex (VOR) from the ideal eye movement angular velocity and the eye rotation angular velocity and determining a sign of sleepiness based on the vestibulo-ocular reflex.

Japanese Patent No. 5255063 discloses a result in which a test is conducted while an experimental task such as fixation of an upper portion of a license plate of the preceding vehicle projected on a screen as a fixation point is imposed on a subject using an experimental system simulating a driving time of a vehicle, namely, a driving simulator system.

However, the pseudo experimental environment using the driving simulator system is greatly different from an actual running environment of the vehicle. The inventor has found that, as a result of verification in the actual running environment of the vehicle (hereinafter, referred to as an actual vehicle environment), a vestibulo-ocular reflex movement is hardly accurately acquired in the actual vehicle environment.

Examples of the eye movements include a saccadic movement (also referred to as an impulsive eye movement) and a congestion movement in addition to the vestibulo-ocular reflex movement. In the experimental environment, the predetermined fixation point is fixated such that the vestibulo-ocular reflex movement is easily generated. However, in the actual vehicle environment, a situation outside the vehicle, a situation of a road surface, a behavior of the vehicle, and the movement of the driver's head and eyes are not constant, and the eye movements other than the vestibulo-ocular reflex movement are generated in a complex manner.

The vestibulo-ocular reflex movement is induced by the head movement. In the experimental environment, the driver's seat is vibrated to induce the head movement. However, in the actual vehicle environment, a vibration state in which the head movement is induced is not necessarily generated. Therefore, it is difficult to determine the sleepiness with high accuracy even if the sleepiness is to be determined based on the vestibulo-ocular reflex movement in the situation in which various types of eye movements are generated or the situation in which the vestibulo-ocular reflex movement is hardly induced. In addition to the actual vehicle environment, the similar problem may be generated even in various real environments such as an operation environment or a work environment of equipment.

SUMMARY

One or more aspects have been made in view of the above problems, and one or more aspects aim to provide a data processing device, a monitoring system, an awakening system, a data processing method, and a data processing program, which are capable of accurately calculating the sleepiness even in the situation that is not suitable for calculating the sleepiness based on the vestibulo-ocular reflex movement.

In order to achieve the above object, there is provided a data processing device (1) according to the present disclosure that performs data processing of monitoring a person, the data processing device including: a calculator configured to calculate pupil movement and head movement of the person; an evaluator configured to evaluate a suitability degree of a situation in calculating vestibulo-ocular reflex movement based on the pupil movement and the head movement of the person; a provision unit configured to provide the suitability degree evaluated by the evaluator to data relating to the pupil movement and the head movement of the person calculated by the calculator; a selector configured to select a first technique of calculating sleepiness based on the vestibulo-ocular reflex movement of the person or a second technique different from the first technique based on the suitability degree provided to the data; a first sleepiness calculator configured to calculate the sleepiness based on the first technique when the selector selects the first technique; and a second sleepiness calculator configured to calculate the sleepiness based on the second technique when the selector selects the second technique.

In the data processing device (1), the evaluator evaluates the suitability degree of the situation in calculating the vestibulo-ocular reflex movement, and the provision unit provides the suitability degree to the data. Thus, depending on the suitability degree provided to the data, what kind of suitability is owned by the data as the situation in calculating the vestibulo-ocular reflex movement can be discriminated by the suitability degree provided to the data. The selector selects the first technique or the second technique based on the suitability degree, and the sleepiness is calculated based on the selected technique. Consequently, even in the situation that is not suitable for calculating the sleepiness by the first technique, namely, even in the situation that is not suitable for calculating the sleepiness based on the vestibulo-ocular reflex movement of the person, the sleepiness can be calculated based on the second technique, and the sleepiness can accurately be calculated in the real environment.

According to a data processing device (2) of the present disclosure, in the data processing device (1), the selector selects the first technique when the suitability degree satisfies a predetermined condition, and the selector selects the second technique when the suitability degree does not satisfy the predetermined condition.

According to the data processing device (2), in the case where the suitability degree satisfies the predetermined condition, namely, in the case where the data is suitable as the situation in calculating the vestibulo-ocular reflex movement, the first technique is selected, and the sleepiness is calculated based on the vestibulo-ocular reflex movement of the person. On the other hand, in the case where the suitability degree does not satisfy the predetermined condition, namely, even if the data is not suitable as the situation in calculating the vestibulo-ocular reflex movement, the sleepiness is calculated by the second technique. Thus, the calculation accuracy of the sleepiness can be enhanced in the real environment by properly selecting the first technique or the second technique based on the predetermined condition.

According to a data processing device (3) of the present disclosure, in the data processing device (1) or (2), the first sleepiness calculator includes a reflex movement calculator configured to calculate the vestibulo-ocular reflex movement of the person based on the data in consideration of the suitability degree, and the sleepiness is calculated based on the vestibulo-ocular reflex movement of the person calculated by the reflex movement calculator.

In the data processing device (3), the first sleepiness calculator calculates the vestibulo-ocular reflex movement of the person based on the data in consideration of the suitability degree, and the sleepiness is calculated based on the calculated vestibulo-ocular reflex movement of the person. Consequently, using the proper data in which the suitability degree is considered among the pieces of calculated data, the calculation accuracy of the vestibulo-ocular reflex movement of the person can be enhanced, the sleepiness can accurately be calculated based on the vestibulo-ocular reflex movement of the person, and a sign of the sleepiness can also be accurately detected in the real environment.

According to a data processing device (4) of the present disclosure, in the data processing device (1) or (2), the second sleepiness calculator includes a saccadic movement calculator configured to calculate saccadic movement of the person, and the sleepiness is calculated based on the saccadic movement of the person calculated by the saccadic movement calculator.

In the data processing device (4), the second sleepiness calculator calculates the saccadic movement of the person, and the sleepiness is calculated based on the calculated saccadic movement of the person. The saccadic movement is also called an impulsive eye movement, and is a fast and short-duration eye movement that is generated in changing the sight line position. The saccadic movement is greatly different from the low-speed vestibulo-ocular reflex movement in a characteristic. The situation that is not suitable for calculating the vestibulo-ocular reflex movement is, for example, a situation in which the saccadic movement is frequently generated. Thus, even in the situation that is not suitable for calculating the vestibulo-ocular reflex movement, it is possible to accurately calculate the sleepiness by calculating the sleepiness based on the saccadic movement of the person.

According to a data processing device (5) of the present disclosure, in the data processing device (1) or (2), the second sleepiness calculator includes an eyelid movement calculator configured to calculate an index based on eyelid movement of the person, and the sleepiness is calculated based on an index based on the eyelid movement calculated by the eyelid movement calculator.

In the data processing device (5), the second sleepiness calculator calculates the index based on the eyelid movement of the person, and calculates the sleepiness based on the index based on the calculated eyelid movement. Examples of the index based on the eyelid movement of the person include at least one of an eyelid opening degree (an opening degree of eye), a blinking frequency, and a PER-CLOS (Percent of the time eyelids are closed) indicating a proportion of a closed eye time to a unit time. As a result, even in the situation that is not suitable for calculating the vestibulo-ocular reflex movement, the sleepiness can accurately be calculated by calculating the sleepiness based on the index based on the eyelid movement.

In any one of the data processing devices (1) to (5), a data processing device (6) according to the present disclosure further includes an awakening controller configured to perform control of awakening the person based on the sleepiness calculated by the first sleepiness calculator or the second sleepiness calculator.

In the data processing device (6), the awakening controller performs the control of awakening the person based on the sleepiness calculated by the first sleepiness calculator or the second sleepiness calculator, so that the person can be awakened from the sleepiness.

According to a data processing device (7) of the present disclosure, in any one of the data processing devices (1) to (6), the evaluator evaluates the suitability degree based on a state of the person or an object operated by the person.

In the data processing device (7), the suitability degree is evaluated based on the state of the person or the object operated by the person. Thus, by considering the state of the person or the object operated by the person, the suitability can more accurately be evaluated as the situation in calculating the vestibulo-ocular reflex movement, and the suitability degree can more correctly be evaluated. This enables the selector to more properly select the first technique or the second technique to enhance the calculation accuracy of the sleepiness by the first technique or the second technique.

According to a data processing device (8) of the present disclosure, in the data processing device (7), the object is a vehicle and the person is a driver of the vehicle.

In the data processing device (8), the object is a vehicle, and the person is a driver who drives the vehicle, so that the sleepiness of the driver can accurately be calculated in an actual vehicle environment.

According to a data processing device (9) of the present disclosure, in the data processing device (8), the evaluator evaluates the suitability degree based on at least one of a noise component included in the data, a sight line direction of the driver, a running state of the vehicle, and a detection state of the object existing in a traveling direction of the vehicle.

In the data processing device (9), the suitability degree is evaluated based on at least one of the noise component included in the data, the sight line direction of the driver, the running state of the vehicle, and the detection state of the object existing in the traveling direction of the vehicle.

For example, for the small noise component, the data may be evaluated to have the high suitability degree. In the case where the sight line direction of the driver falls within a predetermined forward range, in the case where the vehicle runs straight, or in the case where the object is not detected in the traveling direction of the vehicle, the suitability degree may highly be evaluated.

Thus, the suitability degree can more correctly be evaluated in the actual vehicle environment by considering at least one of the noise component included in the data, the sight line direction of the driver, the running state of the vehicle, and the detection state of the object existing in the traveling direction of the vehicle. This enables the selector to more properly select the first technique or the second technique to enhance the calculation accuracy of the sleepiness by the first technique or the second technique. The noise component included in the data includes the eye or head movement components disturbing the calculation of the vestibulo-ocular reflex movement, and, for example, includes the component of the eye movement other than the vestibulo-ocular reflex movement.

In the data processing device (8), a data processing device (10) according to the present disclosure further includes an acquisition unit configured to acquire acceleration of the vehicle. The evaluator evaluates the suitability degree based on a relationship between a change in acceleration of the vehicle acquired from the vehicle and the head movement or the pupil movement of the driver calculated by the calculator.

In the data processing device (10), for example, the suitability degree is highly evaluated in the case where the head movement or the pupil movement of the driver is calculated according to the change in acceleration of the vehicle, namely, following the vibration generated in the vehicle. Thus, the condition that the vestibulo-ocular reflex movement is easily generated is properly evaluated in the actual vehicle environment, and the suitability degree can correctly be evaluated. This enables the selector to more properly select the first technique or the second technique to enhance the calculation accuracy of the sleepiness by the first technique or the second technique.

A monitoring system (1) according to the present disclosure includes: any one of the data processing devices (1) to (10); and an imaging device configured to capture an image including the person. The calculator of the data processing device calculates the pupil movement and the head movement of the person using the image acquired from the imaging device.

Because the monitoring system (1) includes any one of the data processing devices (1) to (10) and the imaging device, a system that is easily introduced in various real environments can be obtained, one of the effects of the data processing devices (1) to (10) being obtained in the system.

An awakening system according to the present disclosure includes: the data processing device (6); and an awakening device controlled by the awakening controller of the data processing device (6). In the awakening system, the awakening controller controls the awakening device, so that the awakening device can properly awaken the person.

A data processing method according to the present disclosure is a data processing method for monitoring a person, the method including:

a calculation step of calculating pupil movement and head movement of the person;

an evaluation step of evaluating a suitability degree of a situation in calculating vestibulo-ocular reflex movement based on the pupil movement and the head movement of the person;

a provision step of providing the suitability degree evaluated in the evaluation step to data relating to the pupil movement and the head movement of the person calculated in the calculation step;

a selection step of selecting a first technique of calculating sleepiness based on the vestibulo-ocular reflex movement of the person or a second technique different from the first technique based on the suitability degree provided to the data;

a first sleepiness calculation step of calculating the sleepiness based on the first technique when the first technique is selected in the selection step; and a second sleepiness calculation step of calculating the sleepiness based on the second technique when the second technique is selected in the selection step.

In the data processing method, the suitability degree of the situation in calculating the vestibulo-ocular reflex movement is evaluated in the evaluation step, and the suitability degree is provided to the data in the provision step. Thus, depending on the suitability degree provided to the data, what kind of suitability is owned by the data as the situation in calculating the vestibulo-ocular reflex movement can be discriminated by the suitability degree provided to the data. Through the selection step, the first technique or the second technique is selected based on the suitability degree, and the sleepiness is calculated based on the selected technique. Consequently, even in the situation that is not suitable for calculating the sleepiness by the first technique, namely, even in the situation that is not suitable for calculating the sleepiness based on the vestibulo-ocular reflex movement of the person, the sleepiness can be calculated based on the second technique, and the sleepiness can accurately be calculated in the real environment.

A data processing program according to the present disclosure is a data processing program causing at least one computer to perform data processing of monitoring a person, the data processing program causing the at least one computer to perform:

a calculation step of calculating pupil movement and head movement of the person;

an evaluation step of evaluating a suitability degree of a situation in calculating vestibulo-ocular reflex movement based on the pupil movement and the head movement of the person;

a provision step of providing the suitability degree evaluated in the evaluation step to data relating to the pupil movement and the head movement of the person calculated in the calculation step;

a selection step of selecting a first technique of calculating sleepiness based on the vestibulo-ocular reflex movement of the person or a second technique different from the first technique based on the suitability degree provided to the data;

a first sleepiness calculation step of calculating the sleepiness based on the first technique when the first technique is selected in the selection step; and a second sleepiness calculation step of calculating the sleepiness based on the second technique when the second technique is selected in the selection step.

In the data processing program, the suitability degree of the situation in calculating the vestibulo-ocular reflex movement is evaluated in the evaluation step, and the suitability degree is provided to the data in the provision step. Thus, depending on the suitability degree provided to the data, what kind of suitability is owned by the data as the situation in calculating the vestibulo-ocular reflex movement can be discriminated by the suitability degree provided to the data. Through the selection step, the first technique or the second technique is selected based on the suitability degree, and the sleepiness is calculated based on the selected technique. Consequently, the data processing device can be constructed in which the sleepiness can be calculated by the second technique and the sleepiness in the real environment can accurately be calculated even in the situation that is not suitable for calculating the sleepiness by the first technique, namely, even in the situation that is not suitable for calculating the sleepiness based on the vestibulo-ocular reflex movement of the person.

DETAILED DESCRIPTION

Embodiments of a data processing device, a monitoring system, an awakening system, a data processing method, and a data processing program will be described below with reference to the drawings. For example, the data processing device according to one or more embodiments is widely applicable to a system that monitors a person (subject). For example, in addition to a system that monitors drivers (operators) of various moving bodies such as vehicles, railroad vehicles, airplanes, and ships, the data processing device can also be applied to a system that monitors a person who operates and monitors various types of equipment such as machines and devices in the factory and performs predetermined work.

[System Configuration Example]

Figure 1:
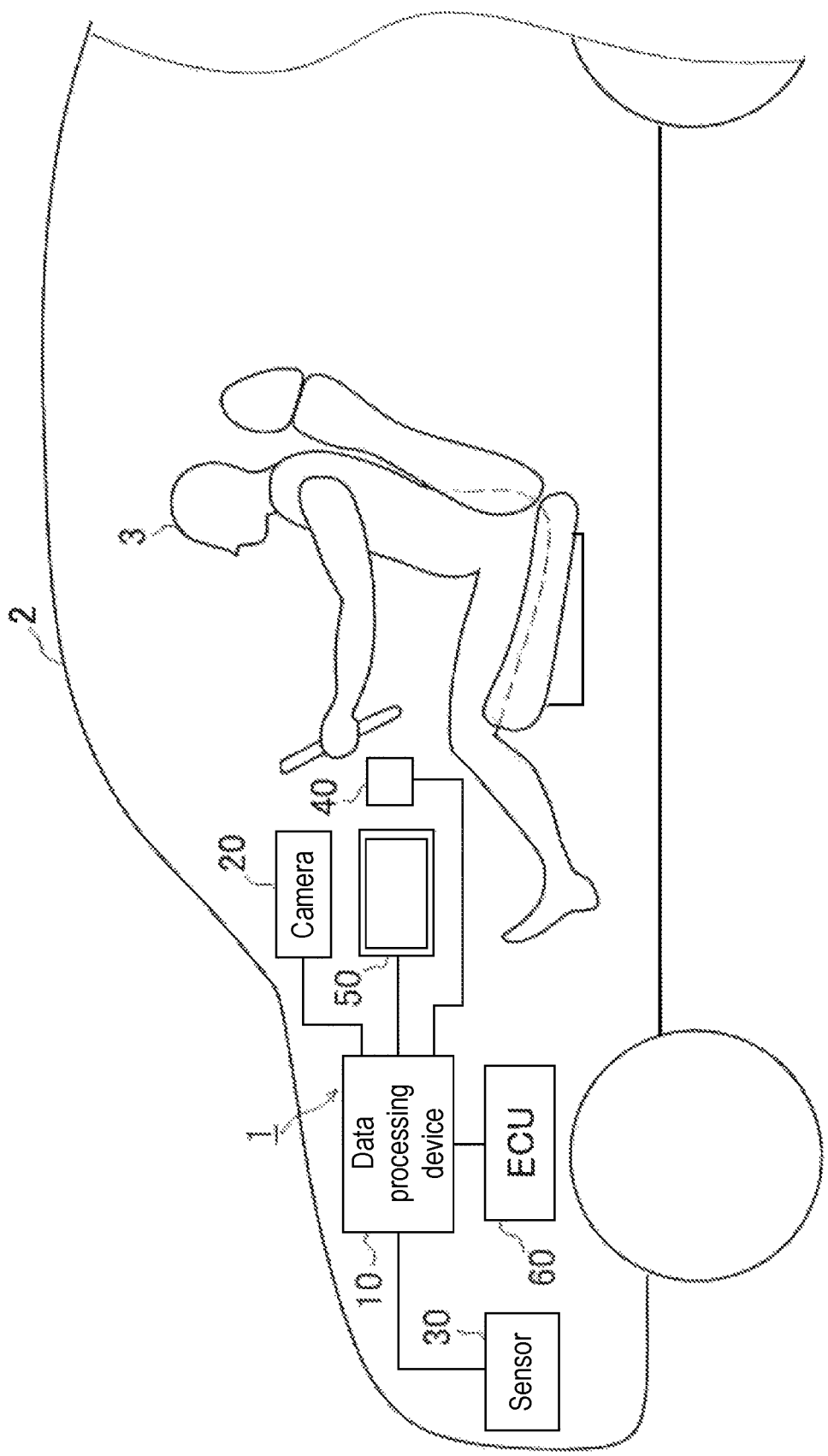
FIG. 1 is a diagram schematically illustrating an example of a monitoring system using a data processing device according to one or more embodiments.

FIG. 1 is a view schematically illustrating an example of a monitoring system using a data processing device according to one or more embodiments. A monitoring system 1 is a driver monitoring system mounted on a vehicle 2, and includes a data processing device 10 and a camera 20. The data processing device 10 is a computer that performs data processing in order to monitor a driver 3 of the vehicle 2. The camera 20 is an example of the "imaging device" of one or more embodiments. The camera 20 is connected to the data processing device 10, and arranged so as to be able to capture an image including a face of the driver 3.

The vehicle 2 is an automobile. However, the vehicle 2 may be a vehicle such as a two-wheeled vehicle, and a type of the vehicle 2 is not particularly limited. The vehicle 2 may be a vehicle (a so-called manual driving vehicle) with a level 0 (no driving automation) at an automatic driving level presented by the American Automotive Engineers Association (SAE) or an automatic driving vehicle. The automatic driving vehicle may be equipped with one of a level 1 (driver assistance), a level 2 (partial automatic driving), a level 3 (conditional automatic driving), a level 4 (advanced automatic driving), and a level 5 (fully automatic driving) in the automatic driving level presented by the SAE.

The data processing device 10 is configured to be connectable to various devices, such as an in-vehicle sensor 30, a starting switch 40, and a navigation device 50, which are mounted on the vehicle 2. The data processing device 10 may be configured to be connectable to at least one Electronic Control Unit (ECU) 60 that controls each unit such as a driving unit, a braking unit, a steering unit, and a suspension unit of the vehicle 2. For example, the starting switch 40 is an ignition switch.

The data processing device 10 aims to enhance the calculation accuracy of the sleepiness of the driver 3 in the actual vehicle environment as an example of the real environment.

As described in the section of the background, in the actual vehicle environment, the situation outside the vehicle, the situation of the road surface, the behavior of the vehicle, the movement of the driver's head and eyes, and the like are not constant. For this reason, data of the pupil movement and the head movement of the driver includes components such as a saccadic movement and a congestion movement (also referred to as noise components), which are different from a component of the vestibulo-ocular reflex movement (also referred to as signal component), in a complex manner. In the actual vehicle environment, the head movement that induces the vestibulo-ocular reflex movement is not always generated.

As a result, a situation in which a signal-noise (SN) ratio of data detecting the vestibulo-ocular reflex movement decreases is also generated in the actual vehicle environment. In this situation, even if sleepiness is calculated based on the vestibulo-ocular reflex movement, there has been a problem in that the sleepiness is hardly calculated with high accuracy. The vestibulo-ocular reflex movement (hereinafter also referred to as "VOR") is eye movement induced by head movement of a person, and is involuntary eye movement that suppresses blurring of a retinal image by moving the eye in a direction opposite to the head movement.

In order to solve this problem, the data processing device 10 of one or more embodiments adopts the following configuration. The data processing device 10 acquires a captured image from the camera 20, and calculates at least the pupil movement and the head movement of the driver 3 from the acquired captured image. Based on the pupil movement and head movement of the driver 3, the data processing device 10 evaluates a suitability degree of the situation when calculating the vestibulo-ocular reflex movement.

The suitability degree is evaluated based on at least one of a state of the driver 3 detected from the captured image or a state of the vehicle 2 detected by the in-vehicle sensor 30. The state of the driver 3 includes a sight line direction of the driver 3. For example, the state in which the driver 3 gazes at a specific direction or a specific point is the state in which the eye movement (such as the saccadic movement and the congestion movement) other than the vestibulo-ocular reflex movement is hardly generated, namely, the noise component of the vestibulo-ocular reflex movement becomes small and the S/N ratio easily increases. When the driver 3 is in this state, for example, the state of the driver 3 is determined to be suitable or highly suitable, and the suitability degree is highly evaluated.

The state of the vehicle 2 includes a running state of the vehicle 2, a detection state of an object (such as a person and another vehicle) existing in a traveling direction of the vehicle 2, and the like. The suitability degree may be evaluated based on a relationship between a change in acceleration of the vehicle 2 and the pupil movement or the head movement of the driver 3. For example, in the case where the state of the vehicle 2 is the state in which the head of the driver 3 is easily displaced or vibrated in an up-down, right-left, front-back, yaw, or pitch direction, namely, in the case where the signal component of the vestibulo-ocular reflex movement, particularly a displacement amount tends to be increased, for example, the state of the vehicle 2 is determined to be suitable or highly suitable, and the suitability degree is highly evaluated.

In the case where the state of the vehicle 2 is the running state in which the eye movement (such as the saccadic movement and the congestion movement) other than the vestibulo-ocular reflex movement of the driver 3 is hardly generated, namely, in the case where the noise component of the vestibulo-ocular reflex movement is decreased, specifically, in the case where the vehicle 2 runs on a straight road, for example, the state of the vehicle 2 is determined to be suitable or highly suitable, and the suitability degree is highly evaluated.

The suitability degree evaluated as described above is represented as data that can be recognized by a computer. For example, the suitability degree may be represented by binary data indicating presence or absence of the suitability for calculating the VOR or a level of the suitability, or multi-valued data (for example, ranked or weighted) according to an extent of suitability. For example, the extent of suitability indicates a rate of suitability as the state of calculating the VOR.

The data processing device 10 provides the suitability degree to data (hereinafter, referred to as calculated data) relating to the pupil movement and the head movement of the driver 3, the data being calculated based on the captured image. The data relating to the pupil movement and the head movement of the driver 3 to which the suitability degree is provided may be the data of the pupil movement and the head movement of the driver 3, a value calculated from the data of the pupil movement and the head movement of the driver 3, or a value indicating relevance between the pupil movement and the head movement of the driver 3. For example, the data processing device 10 may provide the suitability degree to a value such as a coefficient indicating a correlation between the pupil movement and the head movement.

Based on the suitability degree provided to the data relating to the pupil movement and the head movement of the driver 3, the data processing device 10 selects a first technique of calculating the sleepiness based on the vestibulo-ocular reflex movement of the driver 3 or a second technique different from the first technique. The second technique may include a plurality of techniques, and a technique suitable for a predetermined condition may be selected from the plurality of techniques.

For example, in the case where the suitability degree satisfies the predetermined condition, the data processing device 10 selects the first technique, and calculates the sleepiness based on the first technique (that is, based on the vestibulo-ocular reflex movement of the driver 3).

For example, the case where the suitability degree satisfies the predetermined condition includes the case where the data in which the suitability degree is highly evaluated (for example, data in which the suitability degree is greater than or equal to the predetermined threshold or data evaluated to have the suitability as the situation of calculating the VOR) is greater than or equal to a predetermined rate among the pieces of calculated data stored for a predetermined time. The case where the suitability degree satisfies the predetermined condition also includes the case where a statistical value (such as an average value and a mode) of the suitability degree provided to the pieces of calculated data stored for the predetermined time is greater than or equal to the predetermined threshold.

On the other hand, in the case where the suitability degree does not satisfy the predetermined condition, the data processing device 10 selects the second technique, and calculates the sleepiness based on the second technique. The second technique is not particularly limited as long as the second technique is different from the first technique of calculating the sleepiness based on the vestibulo-ocular reflex movement. Preferably, a technique capable of accurately calculating the sleepiness is adopted even in the situation in which the vestibulo-ocular reflex movement is hardly induced.

Examples of the second technique include a technique of calculating the sleepiness based on the saccadic movement, a technique of calculating the sleepiness based on an index based on eyelid movement of the driver 3, a technique of calculating the sleepiness based on an change in area of the pupil detected from the captured image, and a technique of calculating the sleepiness based on a change in rate of a longitudinal diameter and a lateral diameter of the pupil detected from the captured image. Examples of the index based on the eyelid movement include at least one of the eyelid opening degree (the opening degree of eye), the blinking frequency, and the PERCLOS indicating a proportion of a closed eye time to a unit time.

For example, the sleepiness calculated by the data processing device 10 is calculated as the data (sleepiness level) corresponding to a degree of sleepiness from a sleepiness sign stage to a doze state. Alternatively, the sleepiness calculated by the data processing device 10 may be calculated as the data indicating the presence or absence of the sleepiness.

In the data processing device 10, the sleepiness can be calculated based on the second technique even in the situation in which the sleepiness is hardly calculated with high accuracy by the first technique, namely, the situation in which the sleepiness is hardly calculated with high accuracy based on the vestibulo-ocular reflex movement of the driver 3. Thus, the sleepiness can always be calculated with high accuracy in the actual vehicle environment where the complicated eye movement and the like are generated.

[Hardware Configuration Example]

Figure 2:
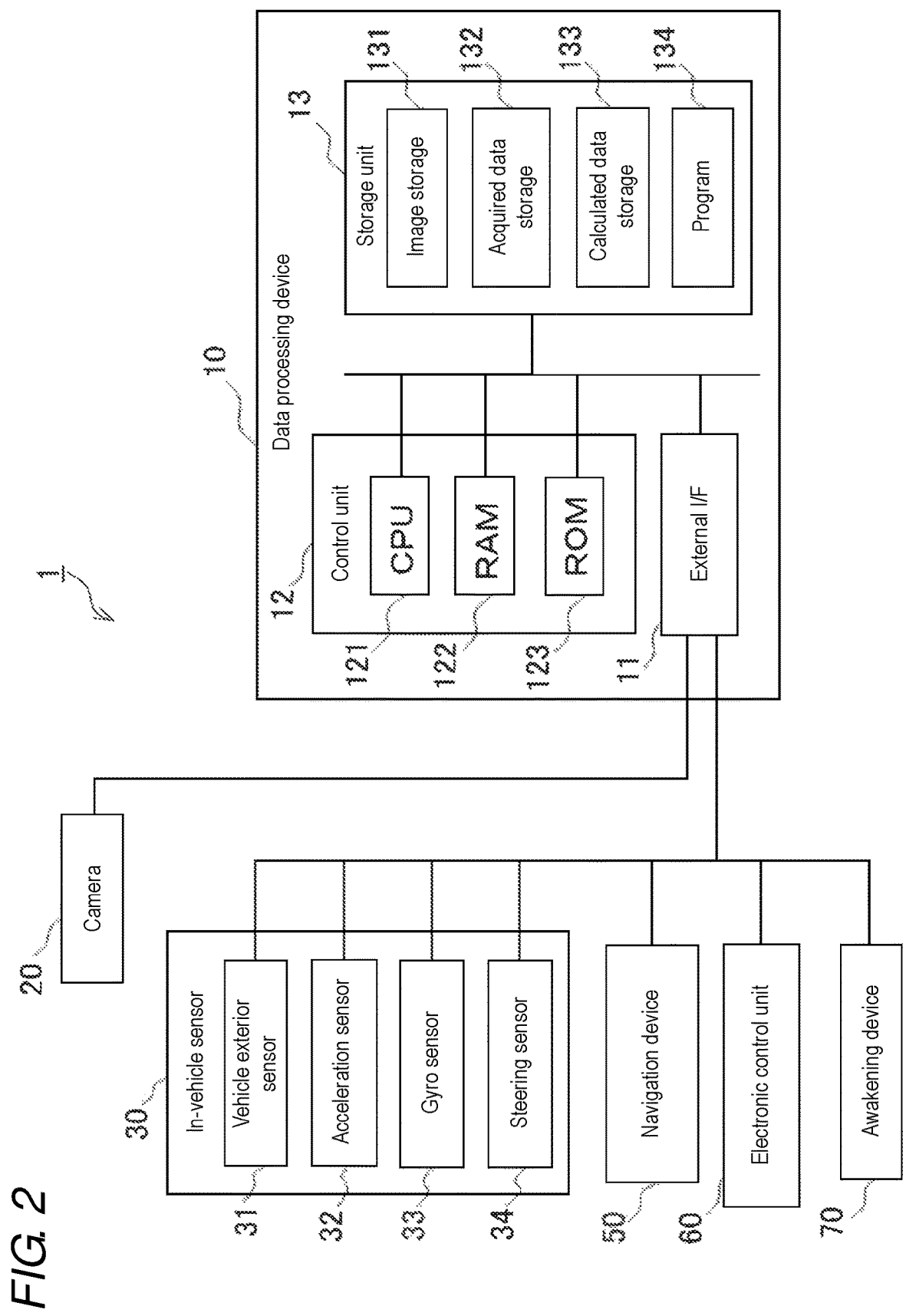
FIG. 2 is a block diagram illustrating an example of a hardware configuration of a monitoring system of one or more embodiments.

FIG. 2 is a block diagram illustrating a hardware configuration example of the monitoring system 1 of one or more embodiments. The monitoring system 1 includes the data processing device 10 and the camera 20.

The data processing device 10 is constructed with a computer to which an external interface (also referred to as an external I/F) 11, a control unit 12, and a storage unit 13 are electrically connected. The control unit 12 includes a Central Processing Unit (CPU) 121 that is a hardware processor, a Random Access Memory (RAM) 122, and a Read Only Memory (ROM) 123, and performs various kinds of control according to data processing. The control unit 12 may include a plurality of hardware processors. In addition to the CPU 121, the hardware processor may include a microprocessor, and a Graphics Processing Unit (GPU).

The storage unit 13 is constructed with at least one storage device, such as the RAM, the ROM, a hard disk drive (HDD), a solid state drive (SSD), a flash memory, and other volatile or nonvolatile memories, which can store data by a semiconductor device.

The storage unit 13 includes an image storage 131, an acquired data storage 132, and a calculated data storage 133. A program 134 is stored in the storage unit 13. The program 134 is a program including an instruction to cause the data processing device 10 to execute various pieces of data processing of monitoring the driver 3. The program 134 may be stored in the ROM 123 of the control unit 12. Each unit of the storage unit 13 may be provided in the RAM 122 of the control unit 12.

The external I/F 11 is an interface that connects the data processing device 10 to various devices mounted on the vehicle 2, and is configured appropriately according to the connected device. For example, the external I/F 11 is connected to the camera 20, the in-vehicle sensor 30, the starting switch 40, the navigation device 50, the electronic control unit 60, and the awakening device 70 through an in-vehicle network such as a Controller Area Network (CAN). The external I/F 11 may be provided in each connected device. A device other than the above devices may be connected to the external I/F 11.

The camera 20 is a device that captures an image including a face of the driver 3. For example, the camera 20 includes a lens unit (not illustrated), an imaging element unit (not illustrated), a light irradiation unit (not illustrated), a controller (not illustrated) that controls these components. For example, the imaging element unit includes an imaging element such as a Charge Coupled Device (CCD) and a Complementary Metal Oxide Semiconductor (CMOS), a filter, and a microlens.

The imaging element unit may include an infrared sensor, such as the CCD, the CMOS, or a photodiode, which can form the captured image by receiving an ultraviolet ray or an infrared ray, in addition to the imaging element capable of receiving light in a visible region to form the captured image.

The light irradiation unit includes a light emitting element such as a Light Emitting Diode (LED), and an infrared LED or the like may be used as the light irradiation unit such that the state of the driver can be captured irrespective of day and night. The controller includes a CPU, a memory, and an image processing circuit.

The controller controls the imaging element unit and the light irradiation unit to output the light (for example, a near infrared ray) from the light irradiation unit, and performs control such that the imaging element unit captures the image using reflected light. The camera 20 captures the image at a predetermined frame rate (for example, 30 to 60 frames per second), and the image data captured by the camera 20 is output to the data processing device 10 and stored in the image storage 131.

Although the camera 20 is constructed with one camera, the camera 20 may be constructed with at least two cameras. The camera 20 may be configured separately from the data processing device 10 (separate casing), or may be integrated with the data processing device 10 (identical casing). The camera 20 may be a monocular camera or a stereo camera.

An installation position of the camera 20 in a passenger compartment is not particularly limited as long as the installation position is a position at which the image of a visual field including at least the face of the driver 3 can be captured. For example, in addition to a vicinity of a center of a dashboard of the vehicle 2, the camera 20 may be installed in a steering portion, a steering column portion, a meter panel portion, a position in the vicinity of a room mirror, an A pillar portion, and the navigation device 50. Information including a specification of the camera 20 (such as an angle of view and a number of pixels (length by width)) and a position posture (such as a mounting angle and a distance from a predetermined origin (such as a handle center position)) may be stored in the camera 20 or the data processing device 10.

The in-vehicle sensor 30 includes a vehicle exterior sensor 31, an acceleration sensor 32, a gyro sensor 33, and a steering sensor 34. Alternatively, the in-vehicle sensor 30 may include other sensors.

The vehicle exterior sensor 31 is a sensor that detects the object existing around the vehicle 2. In addition to a moving object such as another vehicle, a bicycle, and a person, the object may include structures that affect the running of the vehicle 2 including road markings such as white lines, a guardrail, and a median strip. The vehicle exterior sensor 31 is configured to include at least one of a front monitoring camera, a rear monitoring camera, a radar, a Light Detection and Ranging or Laser Imaging Detection and Ranging (LIDAR), and an ultrasonic sensor. Detection data of the object detected by the vehicle exterior sensor 31 may be output to the electronic control unit 60 in addition to being output to the data processing device 10. A stereo camera or a monocular camera can be used as the front monitoring camera and the rear monitoring camera. The radar transmits a radio wave such as a millimeter wave to the surroundings of the vehicle, and detects the position, direction, and distance of the object by receiving the radio wave reflected from the object existing around the vehicle. The LIDAR transmits laser light to the surroundings of the vehicle, and detects the position, direction, and distance of the object by receiving the light reflected from the object existing around the vehicle.

The acceleration sensor 32 is a sensor that detects the acceleration of the vehicle 2. A three-axis acceleration sensor that detects the acceleration in three directions of X, Y, and Z axes, a biaxial acceleration sensor, and a single axis acceleration sensor may be used as the acceleration sensor 32. In addition to the capacitance type, a semiconductor type acceleration sensor such as a piezoresistive type may be used as the three-axis acceleration sensor. Acceleration data detected by the acceleration sensor 32 may be output to the navigation device 50 or the electronic control unit 60 in addition to being output to the data processing device 10.

The gyro sensor 33 is an angular velocity sensor that detects a rotation angular velocity (for example, a yaw rate) of the vehicle 2. A signal of the rotation angular velocity detected by the gyro sensor 33 may be output to the navigation device 50 or the electronic control unit 60 in addition to being output to the data processing device 10.

The steering sensor 34 is a sensor that detects a steering amount with respect to the steering wheel of the vehicle 2. For example, the steering sensor 34 is provided on a steering shaft of the vehicle 2, and detects a steering torque given to the steering wheel by the driver 3 or a steering angle of the steering wheel. A signal, which corresponds to steering operation of the driver 3 and is detected by the steering sensor 34, may be output to the electronic control unit 60 in addition to being output to the data processing device 10.

The navigation device 50 includes a controller (not illustrated), a display (not illustrated), an audio output unit (not illustrated), an operation unit (not illustrated), a map data storage (not illustrated), and a GPS receiver (not illustrated). For example, based on positional information about the vehicle 2 measured by the GPS receiver and map information of the map data storage, the navigation device 50 identifies the road and the lane on which the vehicle 2 runs, calculates a route from a current position of the vehicle 2 to a destination, displays the route on the display, and outputs sound such as route guidance from the sound output unit. The positional information about the vehicle 2, the information about the running road, and the information about the planned running route, which are obtained by the navigation device 50, are outputted to the data processing device 10.

The electronic control unit 60 is constructed with at least one computer device that controls each unit of the vehicle 2, such as the driving unit, the braking unit, the steering unit, and the suspension unit of the vehicle 2. The data processing device 10 stores the data acquired from the in-vehicle sensor 30, the navigation device 50, and the electronic control unit 60 in the acquired data storage 132.

The awakening device 70 is a device controlled by the data processing device 10, and performs operation to awaken the driver 3 based on a control signal from the data processing device 10. For example, the awakening device 70 may be constructed with an alarm device that issues an alarm to the driver 3 by sound or light. Alternatively, the awakening device 70 may be constructed with an air conditioner that blows cold air, warm air, or gas containing an aroma component or an odor component to the driver 3. Alternatively, the awakening device 70 may be constructed with a vibrating device that vibrates a steering wheel, a seat belt, a seat, or the like.

[Functional Configuration Example]

Figure 3:
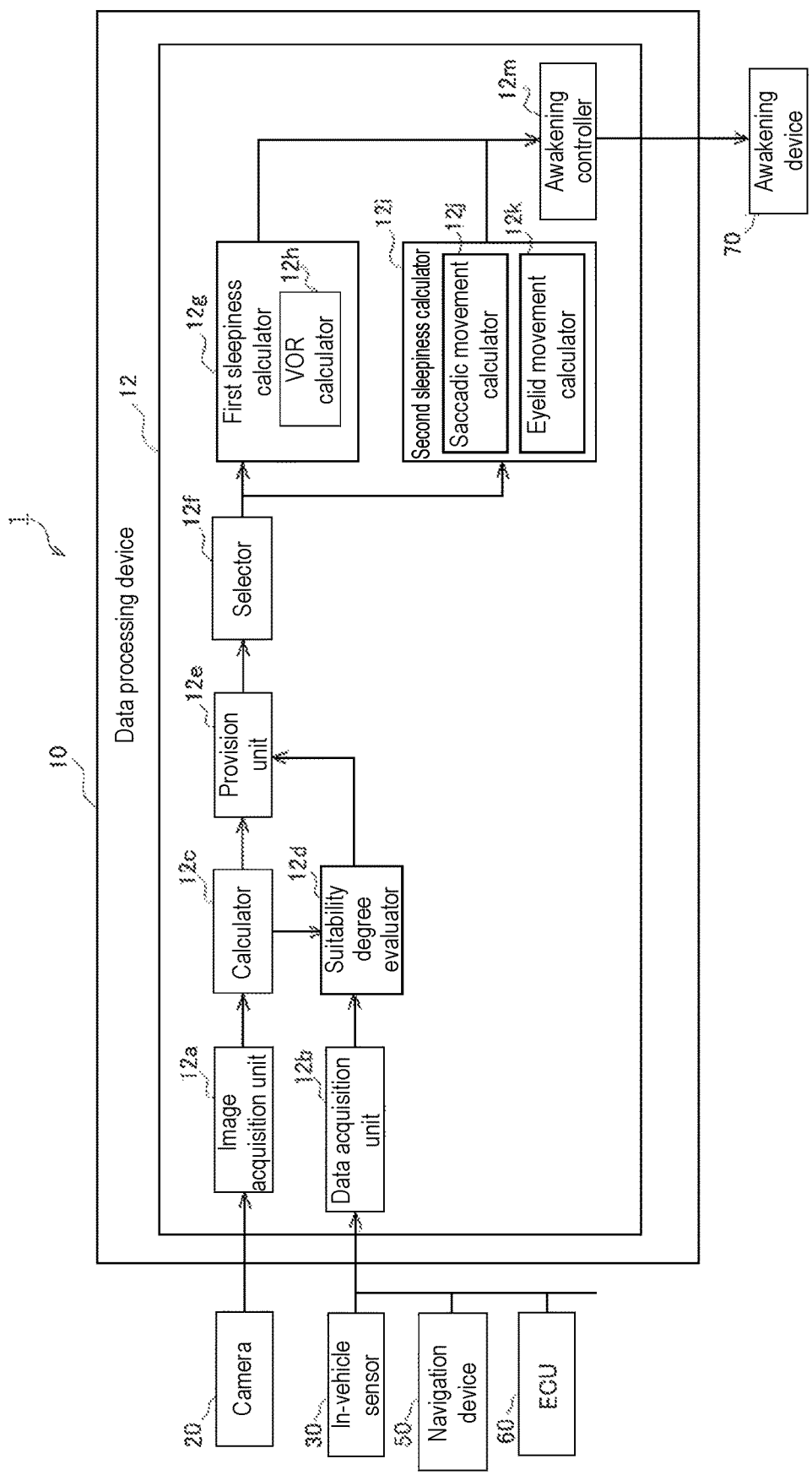
FIG. 3 is a block diagram illustrating an example of a functional configuration of a data processing device of one or more embodiments.

FIG. 3 is a block diagram illustrating an example of a functional configuration of the control unit 12 in the data processing device 10 of one or more embodiments.

The control unit 12 of the data processing device 10 develops the program 134 stored in the storage unit 13 of FIG. 2 in the RAM 122. The control unit 12 interprets and executes the program 134 developed in the RAM 122 using the CPU 121, thereby controlling each component. Consequently, the data processing device 10 is constructed as the computer in which the control unit 12 includes an image acquisition unit 12a, a data acquisition unit 12b, a calculator 12c, a suitability degree evaluator 12d, a provision unit 12e, a selector 12f, a first sleepiness calculator 12g, a VOR calculator 12h, a second sleepiness calculator 12i, a saccadic movement calculator 12j, an eyelid movement calculator 12k, and an awakening controller 12m in FIG. 3. These units provided in the control unit 12 may be configured as software modules.

The image acquisition unit 12a acquires the captured image from the camera 20. The data of the captured image acquired by the image acquisition unit 12a is output to the calculator 12c. The data of the captured image acquired by the image acquisition unit 12a may be stored in the image storage 131, and output from the image storage 131 to the calculator 12c.

The data acquisition unit 12b acquires the data indicating the state of the vehicle 2 from the in-vehicle sensor 30, the starting switch 40, the navigation device 50, the electronic control unit 60, and the like. The data, which indicates the state of the vehicle 2 and is acquired by the data acquisition unit 12b, is output to the suitability degree evaluator 12d. The data, which indicates the state of the vehicle 2 and is acquired by the data acquisition unit 12b, may be stored in the acquired data storage 132, and output from the acquired data storage 132 to the suitability degree evaluator 12d.

The calculator 12c performs processing of calculating the pupil movement and the head movement of the driver 3. In one or more embodiments, the pupil movement and the head movement of the driver 3 are calculated by image analysis of the captured image acquired from the camera 20. For example, the calculation processing is performed in each frame of the captured image. Alternatively, the calculation processing may be performed at predetermined frame intervals.

An example of the pupil movement calculation processing performed by the calculator 12c will be described below. The calculator 12c detects the face (for example, a face region) of the driver 3 from the image captured by the camera 20 by template matching. The face region may be detected using a template image of a previously-prepared face. Subsequently, the calculator 12c detects the position of the pupil from the face region of the driver 3 by performing the template matching on the face region of the driver 3 detected from the captured image. The position of the pupil may be detected using the previously-prepared template image of the pupil. The calculator 12c detects the position of the pupil of the driver 3 in each frame of the captured image, and calculates the pupil movement (for example, eye movement angular velocity) from the position change (movement amount) of the pupil for each frame.

An example of the head movement calculation processing performed by the calculator 12c will be described below. The calculator 12c detects the face (for example, a face region) of the driver 3 from the image captured by the camera 20 by the template matching. The face region may be detected using a template image of a previously-prepared face. The data of the face region of the driver 3 detected by the above processing of calculating the pupil movement may be used.

Subsequently, the calculator 12c detects the position of the eye from the face region by performing the template matching on the face region of the driver 3 detected from the captured image. The position of the eye may be detected using the previously-prepared template image of the eye. In the template image of the eye, for example, coordinates indicating the positions of the outer corner of the eye and the inner corner of the eye are previously linked to each other. The positions of the outer and inner corners of the eye of the driver 3 in the captured image can be detected from the coordinates of the outer and inner corners of the eye in the template image of the eye. Because the positions of the outer and inner corners of the eye do not move due to opening and closing movement of the eye such as blinking, the position changes of the outer and inner corners of the eye are assumed to be moved by the head movement. The calculator 12c detects the positions of the outer and inner corners of the driver 3 in each frame of the captured image, and calculates the head movement (for example, head movement angular velocity) from the position changes (movement amount) of the outer and inner corners of the eye for each frame. The position of the outer corner of the eye or the inner corner of the eye may be detected.

In addition to the use of two-dimensional image data, the positions of the outer and inner corners of the eye of the driver 3 may be detected from the captured image in combination with distance image data including three-dimensional positional information. In order to acquire the distance image data, for example, the monitoring system 1 may be equipped with a three-dimensional image measuring unit. The three-dimensional image measuring unit is configured to acquire a three-dimensional image (distance image) in which each pixel of the captured image has a value (information about a depth) of the distance to the object. For example, the three-dimensional image measuring unit may be a passive type measuring unit such as a stereo method or an active type measuring unit of a system that projects light such as optical radar or pattern light.

Whether the position changes of the outer and inner corners of the eye of the driver 3 are caused by parallel movement (up-down or right-left movement) or rotation movement (movement in the yaw or pitch direction) of the head can accurately be detected by combining the two-dimensional image and the distance image in this way. With this configuration, the pupil movement and the head movement can more accurately be calculated, and the monitoring accuracy of the vestibulo-ocular reflex movement can further be enhanced.

The processing of calculating the pupil movement and the head movement of the driver 3 is not limited to the above example, but various known techniques can be adopted. For example, as disclosed in International Publication No. 2006/051607 and Japanese Unexamined Patent Publication No. 2007-249280, a feature point of each organ (such as eyes, a mouth, a nose, and ears) of a face is detected in each frame of the image, a direction of the face is obtained from the position of the feature point of each organ of the face, and the head movement may be calculated from the change (movement amount) of the direction of the face in each frame.

In addition to the configuration that calculates the pupil movement and the head movement of the driver 3 in each frame, the calculator 12c may include the configuration that calculates an area (the number of pixels) of the pupil detected from the captured image in each frame or the configuration that calculates a ratio between the longitudinal diameter and the lateral diameter (longitudinal diameter/lateral diameter) of the pupil detected from the captured image. The calculator 12c may include the configuration that calculates information about the sight line direction and the opening and closing of the eyes. The pupil movement of the driver 3 is calculated by the image analysis of the captured image acquired from the camera 20, and the head movement of the driver 3 may be calculated based on the data acquired from a gyro sensor or the like attached to the head of the driver 3. The data (calculated data), which relates to the pupil movement and the head movement of the driver 3 and is calculated by the calculator 12c, is output to the provision unit 12e and the suitability degree evaluator 12d.

The suitability degree evaluator 12d takes in the data, which indicates the state of the vehicle 2 and is acquired by the data acquisition unit 12b, and the data, which indicates the state of the driver 3 and is calculated by the calculator 12c, and performs the processing of evaluating the suitability degree of the situation using these pieces of data when the vestibulo-ocular reflex movement of the driver 3 is calculated. For example, the suitability degree evaluator 12d evaluates the suitability degree by determining whether the state of the driver 3 or the state of the vehicle 2 is in a predetermined state suitable for the calculation of the vestibulo-ocular reflex movement.

The above predetermined state includes the state in which the head of the driver 3 is easily vibrated, namely, the state in which a signal component of the vestibulo-ocular reflex movement, particularly the displacement amount increases. More specifically, the predetermined state includes the state in which the head of the driver 3 is easily displaced or vibrated in the up-down direction, the right-left direction, the front-rear direction, or in the yaw or pitch direction.

The predetermined state also includes the state in which the eye movement (for example, the saccadic movement or the congestion movement) other than the vestibulo-ocular reflex movement is hardly generated, namely, the state in which the noise component of the vestibulo-ocular reflex movement becomes small. More specifically, the predetermined state includes the state in which the vehicle 2 runs on a straight road, or the state in which the driver 3 gazes at a specific point.

An example of the processing performed by the suitability degree evaluator 12d will be described below.

(1) The suitability degree evaluator 12d determines whether the pupil movement and the head movement of the driver 3 can be calculated by the calculator 12c. Unless the pupil movement and the head movement are properly calculated, the vestibulo-ocular reflex movement cannot be calculated.

In the case where the calculated data is acquired from the calculator 12c, the suitability degree evaluator 12d determines a similarity between the face region extracted from the image by the template matching and the template image of the face or a similarity between the eye region extracted from the image and the template image of the eye. In the case where each similarity is lower than a predetermined threshold, it may be evaluated that the position of the head (the eye, namely, the outer and inner corners of the eye) or the position of the pupil cannot properly be acquired from the image, namely, the calculated data may be evaluated to be unsuitable as the state of calculating the vestibulo-ocular reflex movement (for example, the similarity has no suitability or the suitability is low).

(2) The suitability degree evaluator 12d may determine whether the data of the pupil movement is the data including many noise components such as the eye movement other than the vestibulo-ocular reflex movement, namely, the saccadic movement. For example, in the case where the eye movement such as the rotation speed or the rotation angle of the eye is larger than a predetermined threshold, such as the case where momentum of the pupil is larger than momentum of the head, or in the case where the pupil moves or rotates by following the movement or the rotation direction of the head (that is, in the substantially identical direction), the data of the pupil movement includes many noise components such as the saccadic movement. In such a case, the data of the pupil movement may be evaluated to be unsuitable as the state of calculating the vestibulo-ocular reflex movement.

When the direction of the face moves greatly, because the driver 3 is not in the state of concentrating on a certain direction, the data of the head movement includes many noise components in the case where the head movement such as the rotation speed and the rotation angle of the face is larger than a predetermined threshold. In such a case, the data of the pupil movement may be evaluated to be unsuitable as the state of calculating the vestibulo-ocular reflex movement.

(3) The suitability degree evaluator 12d may acquire the vehicle speed data through the data acquisition unit 12b in accordance with an acquisition cycle of the captured image taken in the calculator 12c, and determine whether the vehicle speed data is smaller than a predetermined speed or whether the vehicle speed data is larger than the predetermined speed. By this determination, whether the data calculated by the calculator 12c is the data suitable for the calculation of the vestibulo-ocular reflex movement, namely, the suitability degree of the situation in calculating the vestibulo-ocular reflex movement (for example, the presence or absence of the suitability, the suitability degree according to the binary determination such as the level of the suitability, or the suitability degree by the multilevel determination such as the rate of suitability) can be evaluated.

In the case where the vehicle speed is high, generally, the driver 3 tends to concentrate on a narrow forward range. On the other hand, in the case where the vehicle speed is low, the driver 3 tends to voluntarily look over a wide range in order to ensure surrounding safety. Preferably, the data of the eye movement and the head movement in the state in which the driver 3 concentrates on observing the narrow range is used in the case where the vestibulo-ocular reflex movement is calculated. The suitability degree evaluator 12d may evaluate that the vehicle speed data is not suitable as the state of calculating the vestibulo-ocular reflex movement in the case where the vehicle speed data is smaller than a predetermined speed (for example, a slow speed), and evaluate that the vehicle speed data is suitable as the state of calculating the vestibulo-ocular reflex movement when the vehicle speed data is larger than the predetermined speed.

The suitability degree evaluator 12d does not perform the binary determination of the suitability with the predetermined speed as the threshold, but may use a weight coefficient weighted according to the vehicle speed as the suitability degree. For example, the weight coefficient is set to 0.2 when the vehicle speed ranges from 0 km/h to 20 km/h during the calculation of the pupil movement and the head movement using the calculator 12c, the weight coefficient is set to 0.5 when the vehicle speed ranges from 20 km/h to 40 km/h, and the weight coefficient is set to 0.8 when the vehicle speed ranges from 40 km/h to 60 km/h, the weight coefficient is set to 1.0 when the vehicle speed is greater than or equal to 60 km/h, and these weight coefficients may be used as the suitability degree.

(4) The suitability degree evaluator 12d may acquire the steering data through the data acquisition unit 12b in accordance with the acquisition cycle of the captured image taken in the calculator 12c, and determine whether the steering data is larger than a predetermined steering angle. By this determination, whether the data calculated by the calculator 12c is the data suitable for the calculation of the vestibulo-ocular reflex movement, namely, the suitability degree of the situation in calculating the vestibulo-ocular reflex movement (for example, the presence or absence of the suitability, the suitability degree according to the binary determination such as the level of the suitability, or the suitability degree by the multilevel determination such as the rate of suitability) can be evaluated.

Preferably, the data of the eye movement and the head movement in the state in which the driver 3 concentrates on observing the front narrow range is used in the case where the vestibulo-ocular reflex movement is calculated. A tendency for the driver 3 to concentrate on the forward narrow range is high in the case where the vehicle 2 runs on the straight road rather than the case where the vehicle 2 runs on a road with continuous curves. The suitability degree evaluator 12d may evaluate the steering data to be unsuitable as the state of calculating the vestibulo-ocular reflex movement in the case where the steering data is larger than the predetermined steering angle.

(5) The suitability degree evaluator 12d may acquire the position data of the vehicle 2 or the running road data through the data acquisition unit 12b in accordance with the acquisition cycle of the captured image taken in the calculator 12c, and determine whether the vehicle 2 runs currently on the straight road. By this determination, whether the data calculated by the calculator 12c is the data suitable for the calculation of the vestibulo-ocular reflex movement, namely, the suitability degree of the situation in calculating the vestibulo-ocular reflex movement (for example, the presence or absence of the suitability, the suitability degree according to the binary determination such as the level of the suitability, or the suitability degree by the multilevel determination such as the rate of suitability) can be evaluated. The position data of the vehicle 2 or the running road data are acquired from the navigation device 50.

A tendency for the driver 3 to concentrate on the forward narrow range is high in the case where the vehicle 2 runs on the straight road rather than the case where the vehicle 2 runs on a road with continuous curves. In the case where the vehicle 2 does not run on the straight road, the suitability degree evaluator 12d may evaluate that the position data of the vehicle 2 or the running road data are not suitable as the state of calculating the vestibulo-ocular reflex movement.

(6) The suitability degree evaluator 12d may acquire the surrounding monitoring data acquired by the vehicle exterior sensor 31 through the data acquisition unit 12b in accordance with the acquisition cycle of the captured image taken in the calculator 12c, and determine whether an obstacle or a preceding vehicle exists around the vehicle 2. By this determination, whether the data calculated by the calculator 12c is the data suitable for the calculation of the vestibulo-ocular reflex movement, namely, the suitability degree of the situation in calculating the vestibulo-ocular reflex movement (for example, the presence or absence of the suitability, the suitability degree according to the binary determination such as the level of the suitability, or the suitability degree by the multilevel determination such as the rate of suitability) can be evaluated.

In the case where the preceding vehicle or the obstacle moving relative to the vehicle 2 exists, the driver 3 has a tendency to visually follow the relatively moving preceding vehicle or obstacle, and the eyes of the driver 3 move actively. The state in which the eyes move actively is not in the state suitable for calculating the vestibulo-ocular reflex movement. For this reason, in the case where the preceding vehicle or the obstacle moving relative to the vehicle 2 is detected, the suitability degree evaluator 12d may evaluate that the case where the preceding vehicle or the obstacle moves relative to the vehicle 2 is not suitable as the state of calculating the vestibulo-ocular reflex movement.

(7) The suitability degree evaluator 12d may acquire the direction of the sight line of the driver 3 from the calculator 12c, and evaluate whether the data calculated by the calculator 12c is the data suitable for the calculation of the vestibulo-ocular reflex movement, namely, the suitability degree of the situation in calculating the vestibulo-ocular reflex movement (for example, the presence or absence of the suitability, the suitability degree according to the binary determination such as the level of the suitability, or the suitability degree by the multilevel determination such as the rate of suitability) based on the direction of the sight line of the driver 3. A known sight line detection method is adopted as a method for evaluating the direction of the sight line of the driver 3 from the image in which the face of the driver 3 is captured.

For example, in the case where the driver 3 looks at a distant forward place such as a direction of the horizon, there is a high possibility that the driver 3 concentrates on looking at the front. For example, in the case where the direction of the sight line falls within a predetermined angle (for example, ±5 degrees in the vertical direction or ±5 degrees in the right-left direction) with respect to the front direction (reference direction) of the vehicle, the case where the driver 3 looks at the distant forward place may be evaluated to be suitable as the state in which the driver 3 concentrates on the front, namely, the state of calculating the vestibulo-ocular reflex movement.

In the case where the driver 3 looks at the operation unit or the display in the vehicle such as the navigation device 50, there is a high possibility that the driver 3 gazes at the narrow range carefully. Thus, for example, the case where the direction of the sight line of the driver 3 is the installation direction of the navigation device 50 or the like may be evaluated to be suitable as the state of calculating the vestibulo-ocular reflex movement. However, the case where the vestibulo-ocular reflex movement is calculated from the calculated data in gazing at the equipment in the vehicle carefully is preferably applied to the automatic driving vehicle having the automatic driving level of an SAE level 3 or more from the viewpoint of safety.

(8) The suitability degree evaluator 12*d* may evaluate the suitability degree of the situation in calculating the vestibulo-ocular reflex movement by determining whether the data is suitable for calculating the vestibulo-ocular reflex movement based on the momentum (parallel movement or rotational movement) of the head movement calculated by the calculator 12*c*. The vestibulo-ocular reflex movement is the eye movement that is not generated unless the head of the driver 3 moves. Thus, the suitability degree evaluator 12*d* may evaluate that the case where the momentum (parallel movement or rotational movement) of the head movement calculated by the calculator 12*c* is smaller than predetermined momentum is not suitable as the state of calculating the vestibulo-ocular reflex movement.

(9) The suitability degree evaluator 12*d* may acquire the acceleration data of the vehicle 2 through the data acquisition unit 12*b* in accordance with the acquisition cycle of the captured image taken in the calculator 12*c*, and evaluate the suitability degree of the situation in calculating the vestibulo-ocular reflex movement (for example, the presence or absence of the suitability, the suitability degree according to the binary determination such as the level of the suitability, or the suitability degree by the multilevel determination such as the rate of suitability) by determining whether the data calculated by the calculator 12*c* is the data suitable for calculating the vestibulo-ocular reflex movement based on the acceleration data of the vehicle 2. In the case where predetermined acceleration is generated in the up-down, right-left, or front-rear direction of the vehicle 2, the head of the driver 3 moves easily in the up-down, right-left, or pitch direction.

Thus, in the case where the acceleration data of the vehicle 2 is larger than a threshold at which the head movement of the driver 3 is easily generated, the suitability degree evaluator 12*d* may evaluate that the acceleration data of the vehicle 2 is suitable as the state of calculating the vestibulo-ocular reflex movement. The suitability degree evaluator 12*d* may evaluate that the case where the vibration of the vehicle 2 and the head movement, which are obtained from the acceleration data of the vehicle 2, have a certain relationship such as the vibration at an identical frequency in the identical direction is suitable as the state of calculating the vestibulo-ocular reflex movement. In addition to the use of the data from the acceleration sensor 32 mounted on the vehicle 2, the acceleration data of the vehicle 2 may be obtained from the speed of the vehicle 2 that is obtained from a time-series change of the distance to the object recognized by the vehicle exterior sensor 31.

As described above, in the case where the suitability degree evaluator 12*d* determines that the data is suitable or highly suitable as the state of calculating the vestibulo-ocular reflex movement, the suitability degree evaluator 12*d* outputs the determination data indicating that the data is suitable or highly suitable to the provision unit 12*e* as the suitability degree. On the other hand, in the case where the suitability degree evaluator 12*d* determines that the data is not suitable or the suitability is low as the state of calculating the vestibulo-ocular reflex movement, the suitability degree evaluator 12*d* outputs the determination data indicating that the data is not suitable or the suitability is low to the provision unit 12*e* as the suitability degree. Alternatively, in the case where the suitability degree evaluator 12*d* evaluates the extent of suitability as the state of calculating the vestibulo-ocular reflex movement, the suitability degree evaluator 12*d* outputs the data indicating the extent of suitability to the provision unit 12*e* as the suitability degree.

The suitability degree evaluator 12*d* may be configured to perform the evaluation of any one of the above (1) to (9), or may be configured to appropriately combine and perform the evaluations of at least two of the above (1) to (9) according to the state of the vehicle 2 or the driver 3. The processing timing is controlled in the calculator 12*c* and the suitability degree evaluator 12*d* such that the suitability degree can be obtained in each image frame used in the calculation of the calculator 12*c*. For example, the suitability degree is evaluated in each image frame in accordance with a taken-in cycle of the captured image in the calculator 12*c*.

In the case where the calculated data calculated by the calculator 12*c* and the suitability degree evaluated by the suitability degree evaluator 12*d* are acquired, the provision unit 12*e* performs processing of providing the suitability degree evaluated by the suitability degree evaluator 12*d* to the data (the calculated data of each image frame) relating to the pupil movement and the head movement of the driver 3 that are calculated by the calculator 12*c*.

The provision unit 12*e* performs processing of storing the data relating to the pupil movement and the head movement of the driver 3 and the suitability degree provided to the data in the calculated data storage 133 while linking the data relating to the pupil movement and the head movement of the driver 3 and the suitability degree provided to the data with each other in each image frame.

For example, the suitability degree may be binary data indicating the presence or absence of the suitability as the state of calculating the VOR, or multi-valued data according to the extent of suitability, namely, weighted multi-valued data. In the case where the multi-valued data corresponding to the extent of suitability is used as the suitability degree, the suitability as the state of calculating the VOR can finely be discriminated by weighting.

When the calculated data for the predetermined time is stored in the calculated data storage 133, the selector 12*f* performs the processing of selecting one of the first technique of calculating the sleepiness based on the vestibulo-ocular reflex movement of the driver 3 and the second technique different from the first technique based on the suitability degree provided to the calculated data for the predetermined time.

For example, the selector 12*f* selects the first technique when the suitability degree satisfies the predetermined condition, and selects the second technique when the suitability degree does not satisfy the predetermined condition. For example, in the case where the suitability degree is the binary data indicating the presence or absence of the suitability, the condition that the data to which the suitability degree indicating the presence of the suitability is provided among the pieces of calculated data for the predetermined time is greater than or equal to a predetermined proportion (for example, 80%) can be set as the predetermined condition. In the case where the suitability degree is the multi-valued data indicating the extent of suitability (the rate of suitability), the condition that the data to which the suitability degree indicating the rate of suitability greater than or equal to a predetermined threshold is provided among the pieces of calculated data for the predetermined time is greater than or equal to a predetermined proportion (for example, 80%) can be set as the predetermined condition.

When the first technique is selected by the selector 12f, the selection signal of the first technique is output to the first sleepiness calculator 12g. On the other hand, when the second technique is selected by the selector 12f, the selection signal of the second technique is output to the second sleepiness calculator 12i.

In the case where the first technique is selected by the selector 12f, the first sleepiness calculator 12g performs the processing of calculating the sleepiness based on the first technique. More specifically, the first sleepiness calculator 12g includes the VOR calculator 12h that calculates the vestibulo-ocular reflex movement of the driver 3 based on the calculated data in consideration of the suitability degree, and performs the processing of calculating the sleepiness based on the calculated vestibulo-ocular reflex movement of the driver 3 calculated by the VOR calculator 12h.

The VOR calculator 12h performs the processing of calculating the vestibulo-ocular reflex movement of the driver 3 using the data in which the suitability degree satisfies the predetermined condition among the pieces of calculated data for the predetermined time read from the calculated data storage 133. Examples of the data in which the suitability degree satisfies the predetermined condition among the pieces of calculated data for the predetermined time include the data to which the suitability degree indicating the suitability is provided, the data in which the suitability degree indicating the rate of suitability degree is greater than the predetermined threshold, and a predetermined number of pieces of data in descending order of the suitability degree indicating the rate of suitability.

The calculated data relating to the vestibulo-ocular reflex movement calculated by the VOR calculator 12h includes at least one of the pieces of data (also referred to as parameters) such as a VOR gain, a residual standard deviation, and a delay time, and the calculated data preferably includes at least the VOR gain. In principle, the VOR gain means a rate of response of the pupil movement (eye rotation angular velocity) with respect to head movement (head rotation angular velocity), and the VOR gain can be expressed by the pupil movement (eye rotation angular velocity) or the head movement (head rotation angular velocity).

For example, the VOR gain can be obtained by least squares estimation using an equation [Mathematical formula 2] as a coefficient G of a regression model of an equation [Mathematical formula 1], in which an objective variable is an eye rotation angular velocity e(t) and an explanatory variable is an ideal eye angular velocity h(t) and a constant term dc. Where $\varepsilon(t)$ is a residual of the regression model, and $\tau$ is a delay time of the eye movement with respect to the ideal eye movement. An angle of the eye movement is obtained based on the data of the pupil movement calculated by the calculator 12c, and the eye rotation angular velocity e(t) can be obtained by differentiating the angle of the eye movement. The ideal eye angular velocity h(t) can be obtained by obtaining an angle of the head movement based on the data of the head movement calculated by the calculator 12c, and the ideal eye angular velocity h(t) can be obtained by differentiating the angle of the head movement. The VOR gain may be calculated for at least one of the front-rear, up-down, right-left, yaw, and pitch directions of the driver 3.

$$e(t) = Gh(t-\tau) + dc + \varepsilon(t) \quad \text{[Mathematical formula 1]}$$

$$G = \frac{N\sum_{t=1}^{N} h(t-\tau)e(t) - \sum_{t=1}^{N} h(t-\tau)\sum_{t=1}^{N} e(t)}{N\sum_{t=1}^{N} h^2(t-\tau) - \left(\sum_{t=1}^{N} h(t-\tau)\right)^2} \quad \text{[Mathematical formula 2]}$$

The residual standard deviation (SDres) can be calculated by the following equation [Mathematical formula 3].

$$SDres = \sqrt{\frac{1}{N-1}\sum_{t=1}^{N}\varepsilon^2(t)} \quad \text{[Mathematical formula 3]}$$

In the VOR gain and the residual standard deviation, data of a first time (for example, tens of seconds or a predetermined number of frames) is set to one segment such that sufficient estimation accuracy is obtained, and a value in each segment may be calculated at every third time shorter than a second time while overlap is provided for the second time shorter than the first time. When the driver 3 feels sleepy, generally, the VOR gain decreases and the residual standard deviation tends to increase. Thus, a rate of change such as the rate of decrease of the VOR gain or a rate of change such as a rate of increase of the residual standard deviation may be obtained in order to accurately determine a sign of the sleepiness.

The first sleepiness calculator 12g calculates the sleepiness of the driver 3 using the calculated data relating to the vestibulo-ocular reflex movement calculated by the VOR calculator 12h. For example, comparison with the predetermined threshold is performed using at least one of parameters of the VOR gain, the residual standard deviation, and the delay time, and the sleepiness level indicating the degree of sleepiness of the driver 3 is calculated. After calculating the sleepiness of the driver 3, the first sleepiness calculator 12g outputs the calculation result of the sleepiness of the driver 3, for example, the sleepiness level to the awakening controller 12m.

In the case where the second technique is selected by the selector 12f, the second sleepiness calculator 12i performs the processing of calculating the sleepiness based on the second technique. More specifically, the second sleepiness calculator 12i includes the saccadic movement calculator 12j and the eyelid movement calculator 12k, and includes the configuration that performs the processing of calculating the sleepiness based on the saccadic movement of the driver 3 calculated by the saccadic movement calculator 12j and the configuration that performs the processing of calculating the sleepiness based on the index based on the eyelid movement calculated by the eyelid movement calculator 12k. For example, the second sleepiness calculator 12i selects the saccadic movement calculator 12j in the case where the data in which the pupil is detected is greater than or equal to a predetermined ratio (for example, 80%) among the pieces of calculated data for the predetermined time, and the second sleepiness calculator 12i selects the eyelid movement calculator 12k in the case where the data in which the pupil is detected is less than the predetermined ratio (for example, 80%).

The saccadic movement calculator 12j performs the processing of calculating the saccadic movement of the driver 3 using the calculated data for the predetermined time read from the calculated data storage 133. The saccadic movement is also called an impulsive eye movement, and is a fast and short-duration eye movement that is generated in changing the sight line position. The time necessary for the saccadic movement is usually as short as about 20 milliseconds to about 70 milliseconds, and the speed of the saccadic movement is said to be usually about 300 degrees/second to 500 degrees/second in terms of a viewing angle. The saccadic movement is a linear eye movement with an eye fixation before and after the eye movement. Thus, the eye movement (that is, the pupil movement), in which the direction of the eye movement is continuously identical for a predetermined time (for example, 20 milliseconds to 70 milliseconds) while the average angular velocity of the predetermined time is greater than or equal to a predetermined value, can be detected as the saccadic movement.

The following processing example can be applied to the sleepiness calculation processing based on the saccadic movement performed by the second sleepiness calculator 12i. In the case where the saccadic movement in the state in which an awakening degree is high and the saccadic movement in the state in which the awakening degree begins to decrease are compared to each other in the actual vehicle environment, when the awakening degree decreases, an amplitude (movement amount) of the eye movement due to the saccadic movement and the movement speed tend to decrease, and the time interval of the saccadic movement tends to be shortened. In other words, in the case where the awakening degree decreases, the saccadic movement having the small amplitudes and the short time interval tends to be frequently generated. Thus, for example, the amplitude (movement amount) of the saccadic movement, the time interval, and a generation frequency per unit time can be used as a feature amount used to calculate the sleepiness based on the saccadic movement.

The saccadic movement calculator 12j evaluates the saccadic movement generated within a predetermined time based on the calculated data for the predetermined time, and obtains the amplitude (movement amount), the time interval, and the number of generation times within the predetermined time of each evaluated saccadic movement.

The second sleepiness calculator 12i calculates the sleepiness based on the amplitude (movement amount), the time interval, and the number of generation times within the predetermined time of the saccadic movement, which are calculated by the saccadic movement calculator 12j. For example, the number of generation times of the saccadic movement, in which the amplitude is less than or equal to a predetermined value and the time interval is less than or equal to a predetermined time, may be obtained, and the sleepiness level indicating the degree of sleepiness may be calculated according to the number of generation times, or the sleepiness level may be determined to be high in the case where the number of generation times is greater than or equal to a predetermined number of generation times.

The eyelid movement calculator 12k calculates an index based on the eyelid movement of the person from the captured image. Examples of the index based on the eyelid movement of the person include the eyelid opening degree (the opening degree of the eye), the blinking frequency, and the PERCLOS.

The eyelid opening degree indicates the opening degree (%) of the eyes. For example, the eyelid opening degree can be expressed by a ratio between the distance from the upper eyelid to the lower eyelid and the diameter in the lateral direction of the iris, which are detected from the captured image. The blinking frequency indicates the number of blinking times in a predetermined time, and the case where the closed eye state detected from the captured image is less than a typical blinking time (for example, 100 milliseconds to 300 milliseconds) is counted as a blink. The closed eye state may be detected as a closed eye state less than or equal to a degree to which the pupil is hidden by the eyelid, for example, a state in which the eyelid opening degree is less than or equal to a predetermined value (for example, 20% or less).

The PERCLOS indicates the proportion of a closed eye time to a unit time. The closed eye time can be indicated as time in which time during which a closed eye state less than or equal to a degree to which the pupil is hidden by the eyelid, for example, a state in which the eyelid opening degree is less than or equal to a predetermined value (for example, 20% or less) or the ratio between the longitudinal diameter and the lateral diameter (longitudinal diameter/lateral diameter) of the pupil is less than or equal to a predetermined value (for example, 0.8 or less) is continued greater than or equal to a predetermined blinking time is accumulated.

The following processing example can be applied to the processing of calculating the sleepiness based on the index based on the eyelid movement, the processing being performed by the second sleepiness calculator 12i. The eyelid movement calculator 12k calculates the index based on the eyelid movement (for example, at least one of the eye eyelid opening degree, the blinking frequency, and the PERCLOS) based on the calculated data for the predetermined time or the data of the captured image for the predetermined time The second sleepiness calculator 12i calculates the sleepiness based on the index based on the eyelid movement, the index being calculated by the eyelid movement calculator 12k. For example, in the case where it is detected within a predetermined time that the state in which the eyelid opening degree (%) is less than or equal to a predetermined value (for example, 20% or less) is continued for the predetermined time, the sleepiness level indicating that the degree of sleepiness is high is calculated. In the case where it is evaluated that the blinking frequency is greater than or equal to a predetermined number within the predetermined time, the sleepiness level indicating that the degree of sleepiness is high may be calculated. The sleepiness level indicating the degree of sleepiness according to the value (%) of the proportion (PERCLOS) of the closed eye time within the predetermined time may be calculated.

The awakening controller 12m performs the processing of outputting a control signal for awakening the driver 3 to the awakening device 70 based on the sleepiness level acquired from the first sleepiness calculator 12g or the second sleepiness calculator 12i. When the awakening device 70 is constructed with the alarm device that issues the alarm to the driver 3 by sound or light, the awakening controller 12m outputs, to the alarm device, a control signal for operating the alarm device for a predetermined period. In the case where the awakening device 70 is constructed with the air conditioner that blows cold air, warm air, or gas containing an aroma component or an odor component to the driver 3, the awakening controller 12m outputs, to the air conditioner, a control signal for operating the air conditioner for a predetermined period. In the case where the awakening device 70 is constructed with the vibrating device that vibrates a steering wheel, a seat belt, a seat, or the like, the awakening controller 12m outputs, to the vibration device, a control signal for operating the vibration device for a predetermined period.

Processing of outputting a control signal for awakening the driver 3 may be performed on the navigation device 50. In this case, the control signal includes a control signal causing the navigation device 50 to output alarm sound or alarm display awakening the driver 3.

[Processing Operation Example]

Figure 4A:
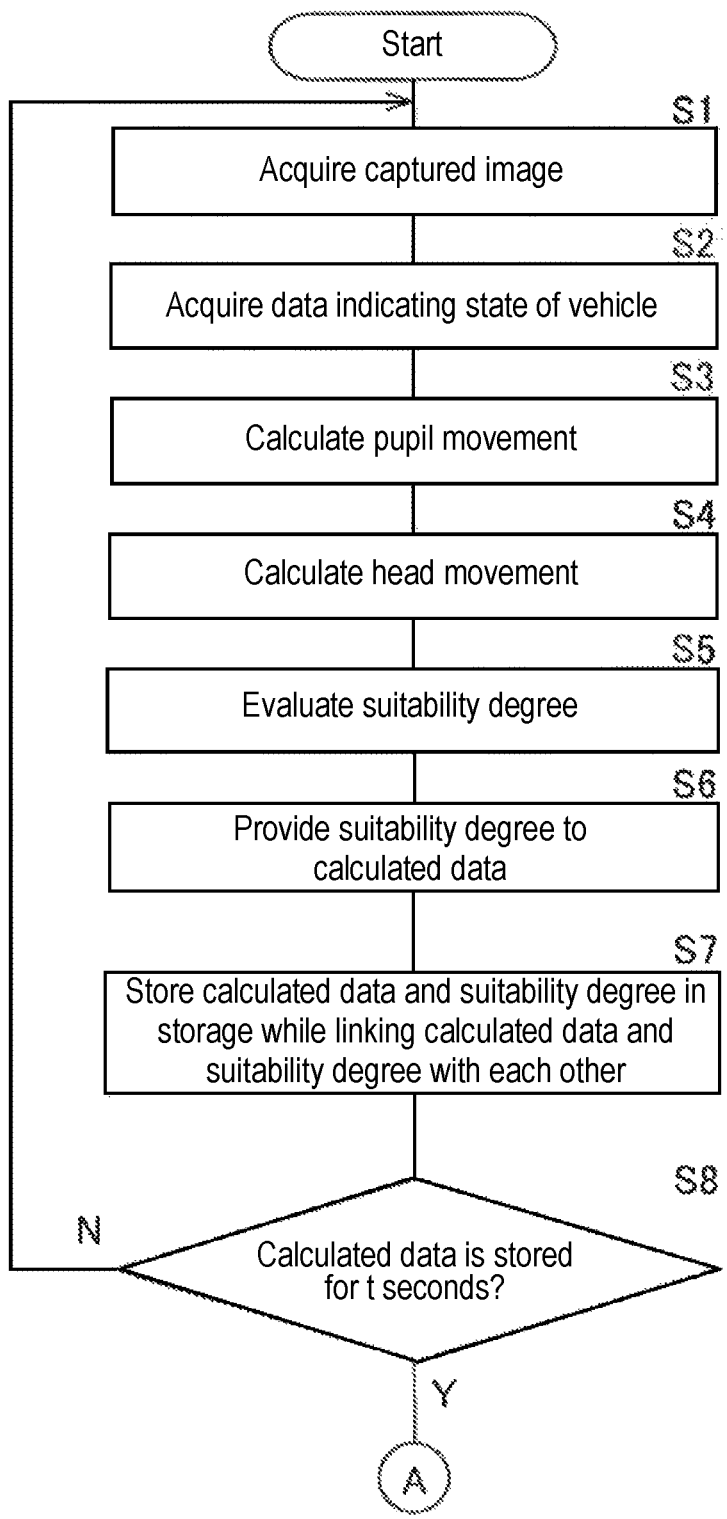
FIG. 4A is a flow diagram illustrating an example of a processing operation performed by a control unit in a data processing device of one or more embodiments.
Figure 4B:
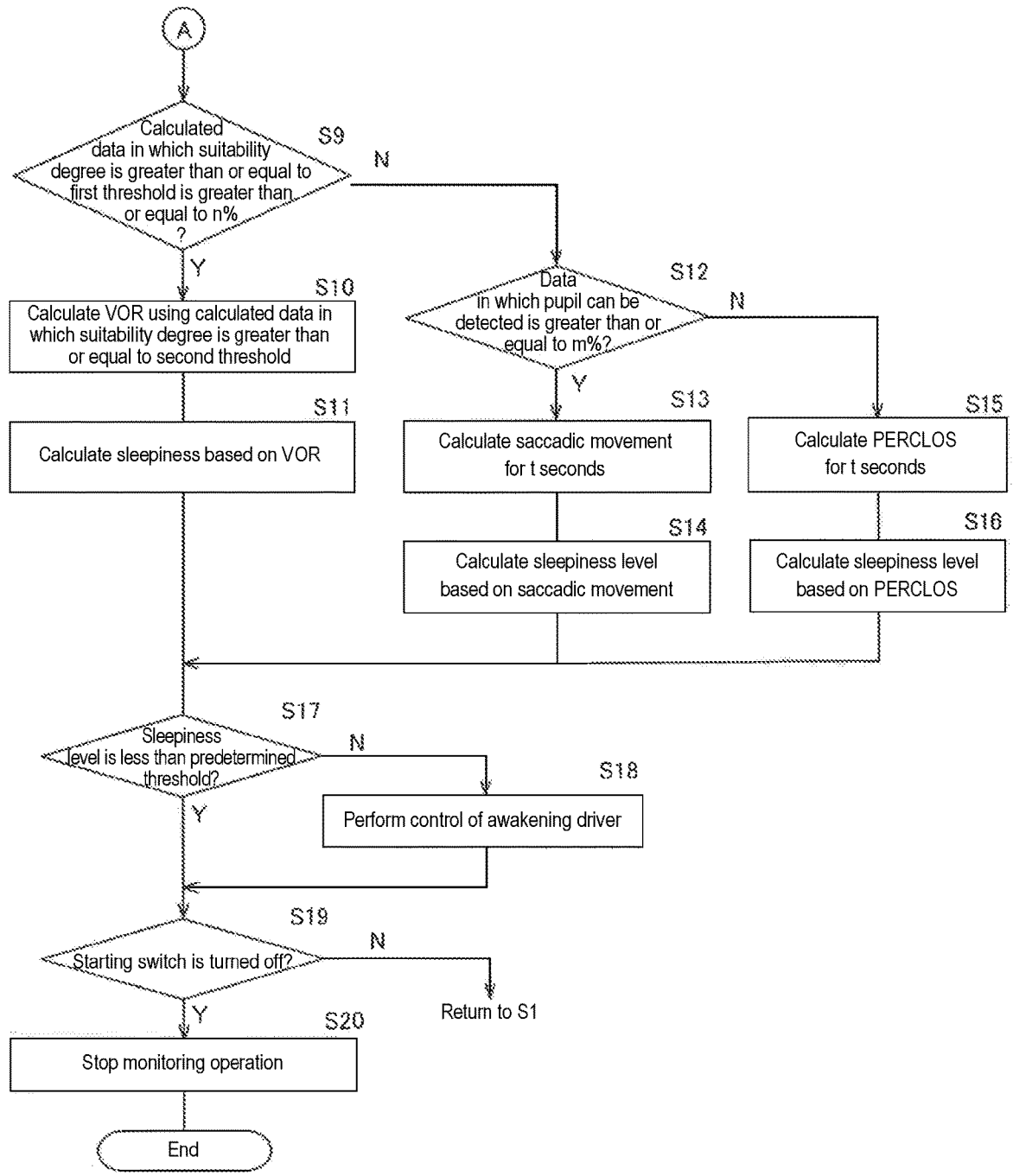
FIG. 4B is a flow diagram illustrating an example of a processing operation performed by a control unit in a data processing device of one or more embodiments.

FIGS. 4A and 4B are flowcharts illustrating an example of the processing operation performed by the control unit 12 in the data processing device 10 of one or more embodiments. The following processing operation is only by way of example, and a change such as omission, replacement, and addition of the processing step can appropriately be made.

(Activation of Monitoring System 1)

When the starting switch 40 of the vehicle 2 is turned on by the driver 3, the data processing device 10 and the camera 20 constituting the monitoring system 1 are activated, and the control unit 12 of the data processing device 10 starts the processing of monitoring the driver 3 based on the program 134.

In step S1, the control unit 12 operates as the image acquisition unit 12a, and performs the processing of acquiring the captured image from the camera 20 disposed so as to capture the image of the face of the driver 3. In the camera 20, images of a predetermined number of frames are captured every second. The control unit 12 acquires these captured images in time series, and performs processing in each frame or each frames at predetermined intervals. Upon acquiring the captured image, the control unit 12 advances the processing to step S2.

In step S2, the control unit 12 operates as the data acquisition unit 12b, and performs the processing of acquiring the data indicating the state of the vehicle 2 from the in-vehicle sensor 30, the navigation device 50, and the like.

For example, the detection data of each sensor may be acquired from the in-vehicle sensor 30, or the road data including the shape (such as the straight line and the curve) of the running road may be acquired from the navigation device 50. Upon acquiring the data indicating the state of the vehicle 2, the control unit 12 advances the processing to step S3.

In step S3, the control unit 12 operates as the calculator 12c, and performs the processing of calculating the pupil movement of the driver 3. The above method is adopted in calculating the pupil movement performed by the calculator 12c. For example, the processing of calculating the pupil movement is performed in each frame of the captured image acquired in step S1. After calculating the pupil movement of the driver 3, the control unit 12 advances the processing to step S4. In step S3, the control unit 12 may calculate a pupil size such as the longitudinal diameter and the lateral diameter or an area of the pupil together with the pupil movement.

In step S4, the control unit 12 operates as the calculator 12c, and performs the processing of calculating the head movement of the driver 3. The above method is adopted in calculating the head movement performed by the calculator 12c. For example, the processing of calculating the head movement is performed in each frame of the captured image acquired in step S1. After calculating the head movement of the driver 3, the control unit 12 advances the processing to step S5. The order of steps S3 and S4 may be changed. The order of step S2 may be changed to be after step S4.

In step S5, the control unit 12 operates as the suitability degree evaluator 12d, and performs the processing of evaluating the suitability degree of the situation in calculating the vestibulo-ocular reflex movement based on the pupil movement and the head movement of the driver 3. In the processing performed by the suitability degree evaluator 12d, the suitability degree may be evaluated by any one of the above methods (1) to (9), or the suitability degree may be evaluated by appropriately combining at least two of the above methods (1) to (9) according to the state of the vehicle 2 or the driver 3. When the suitability degree of the situation in calculating the vestibulo-ocular reflex movement is evaluated, the control unit 12 advances the processing to step S6.

In step S6, the control unit 12 operates as the provision unit 12e, and performs the processing of providing the suitability degree evaluated in step S5 to the data relating to the pupil movement and the head movement calculated in steps S3, S4. When the suitability degree is provided to the data relating to the pupil movement and the head movement of each image frame, the control unit 12 advances the processing to step S7.

In step S7, the control unit 12 performs the processing of storing the data (calculated data) relating to the pupil movement and the head movement calculated in steps S3, S4 and the suitability degree provided to the calculated data in the calculated data storage 133 while linking the data and the suitability degree with each other. After performing the storage processing in the calculated data storage 133, the control unit 12 advances the processing to step S8.

In the case where the pupil size is calculated together with the calculated data in step S3, the control unit 12 stores the calculated data and the data of the pupil size in the calculated data storage 133.

In step S8, the control unit 12 determines whether the calculated data is stored in the calculated data storage 133 for the predetermined time (for example, for t seconds: t seconds indicate several seconds to several tens of seconds. For example, for 40 seconds). Whether the calculated data corresponding to the predetermined number of image frames is stored may be determined instead of the predetermined time.

When determining that the calculated data is not stored in the calculated data storage 133 for t seconds in step S8, the control unit 12 returns to the processing in step S1, and performs the pieces of processing in steps S1 to S7. On the other hand, when determining that the calculated data is stored in the calculated data storage 133 for t seconds in step S8, the control unit 12 advances the processing to step S9 in FIG. 4B.

In step S9, the control unit 12 operates as the selector 12f, reads the calculated data for t seconds from the calculated data storage 133 and the suitability degree, and determines whether the proportion of the calculated data to which the suitability degree higher than the first threshold is provided is greater than or equal to n % (for example, 80% or more) among the pieces of calculated data for t seconds. The first threshold is set as a threshold used to determine the suitability for calculating the sleepiness based on the VOR.

When determining that the proportion of the calculated data to which the suitability degree higher than the first threshold is provided is greater than or equal to n % among the pieces of calculated data for t seconds in step S9, the control unit 12 advances the processing to step S10.

In step S10, the control unit 12 operates as the VOR calculator 12h, and performs the processing of calculating the vestibulo-ocular reflex movement of the driver 3 based on the pieces of calculated data for t seconds in consideration of the suitability degree provided to the calculated data. For example, the vestibulo-ocular reflex movement of the driver 3 is calculated using the calculated data to which the suitability degree higher than the second threshold is provided among the pieces of calculated data for t seconds.

The second threshold may be set to the same value as the first threshold or a different value. However, from the viewpoint of enhancing the calculation accuracy of the VOR, preferably the second threshold is set larger than the first threshold.

The second threshold may be a previously-set threshold value, or may appropriately be changed according to a value, such as an average value, a median value, a mode value, and a standard deviation, which is obtained by statistically processing the suitability degree provided to each calculated data for t seconds. For example, the threshold value may be set higher with increasing average value, median value, or mode value of the suitability degree. For the high average value of the suitability degree, the VOR can accurately be calculated even for the small number of pieces of calculated data, and the efficiency of the calculation processing can also be enhanced. For the large standard deviation of the suitability degree, the threshold is raised, and the calculation accuracy of the VOR can be enhanced using the calculated data to which the high suitability degree is provided.

Examples of the parameter indicating the feature of the vestibulo-ocular reflex movement calculated in step S10 include the VOR gain, the residual standard deviation, and the delay time. After calculating the vestibulo-ocular reflex movement of the driver 3, the control unit 12 advances the processing to step S11.

In step S11, the control unit 12 operates as the first sleepiness calculator 12g, and performs the processing of calculating the sleepiness of the driver 3, for example, the sleepiness level from the vestibulo-ocular reflex movement of the driver 3 calculated in step S10. As described above, the sleepiness level of the driver 3 is calculated using at least one of the parameters such as the VOR gain, the residual standard deviation, and the delay time. After performing the processing of calculating the sleepiness level of the driver 3, the control unit 12 advances the processing to step S17.

On the other hand, when determining that the proportion of the calculated data to which the suitability degree higher than the first threshold is provided is less than n % among the pieces of calculated data for t seconds in step S9, the control unit 12 advances the processing to step S12.

In step S12, the control unit 12 operates as the second sleepiness calculator 12i, and determines whether the proportion of the data in which the pupil is detected (that is, the data indicating the eyelid opening degree to the degree that the pupil is not hidden is greater than or equal to a predetermined proportion (m %) (for example, 80% or more) from among the pieces of calculated data for t seconds.

When determining that the proportion of the data in which the pupil is detected is greater than or equal to m % among the pieces of calculated data for t seconds in step S12, the control unit 12 advances the processing to step S13.

In step S13, the control unit 12 operates as the saccadic movement calculator 12j, and performs the processing of calculating the saccadic movement of the driver 3 based on the pieces of calculated data for t seconds. Examples of the parameter indicating the feature of the saccadic movement calculated in step S13 include the amplitude (movement amount) of the saccadic movement generated in t seconds, the time interval, and the number of generation times in t seconds. After calculating the saccadic movement of the driver 3, the control unit 12 advances the processing to step S14.

In step S14, the control unit 12 operates as the second sleepiness calculator 12i, and performs the processing of calculating the sleepiness, for example, the sleepiness level of the driver 3 based on the saccadic movement of the driver 3 calculated in step S13. As described above, for example, the sleepiness level of the driver 3 is calculated based on the amplitude (movement amount), the time interval, and the number of generation times during t seconds of the saccadic movement. After performing the processing of calculating the sleepiness level based on the saccadic movement, the control unit 12 advances the processing to step S17.

On the other hand, when determining that the proportion of the data in which the pupil is detected is less than m % among the pieces of calculated data for t seconds in step S12, the control unit 12 advances the processing to step S15.

In step S15, the control unit 12 operates as the eyelid movement calculator 12k, and performs the processing of calculating the index based on the eyelid movement of the driver 3 based on the pieces of calculated data for t seconds. At least one of the eyelid opening degree, the blinking frequency, and the PERCLOS can be applied to the index based on the eyelid movement, and the case where the PERCLOS is applied to the index will be described here.

In step S15, the control unit 12 calculates an accumulated time of the closed eye state that is less than or equal to the degree to which the pupil is hidden by the eyelid from the pieces of calculated data for t seconds and the data of the captured image. For example, the closed eye state is detected as a state in which the eyelid opening degree is less than or equal to a predetermined value (for example, 20% or less) or the ratio (longitudinal diameter/lateral diameter) of the longitudinal diameter and the lateral diameter of the pupil is less than or equal to a predetermined value (for example, 0.8 or less). The control unit 12 calculates the accumulated time from the accumulated number of the number of image frames in which the closed eye state is detected, and calculates the proportion ((accumulated time/t seconds)×100 (%)) of the accumulated time to t seconds as the value of the PERCLOS. Subsequently, the control unit 12 advances the processing to step S16.

In step S16, the control unit 12 operates as the second sleepiness calculator 12i, and performs the processing of calculating the sleepiness, for example, the sleepiness level of the driver 3 based on the value of the PERCLOS of the driver 3 calculated in step S15. For example, a sleepiness level table in which the value of the PRECLOS is correlated with the sleepiness level or a relational expression expressing the relationship between the value of the PRECLOS and the sleepiness level is previously stored in the ROM 123 or the program 134, and the sleepiness level corresponding to the calculated value of the PERCLOS value may be obtained from the sleepiness level table or the relational expression. When the sleepiness level is calculated based on the PERCLOS, the control unit 12 advances the processing to step S17.

In step S17, the control unit 12 operates as the awakening controller 12m, and determines whether the sleepiness level detected in step S11, S14, or S16 is smaller than a predetermined threshold (for example, a threshold at which the generation of the sleepiness can be determined). The predetermined threshold value may be one or at least two according to the degree of sleepiness (for example, the degree of sleepiness from the sleepiness sign stage to the doze state). When determining that the sleepiness level is greater than or equal to the predetermined threshold (the sleepiness is generated) in step S17, the control unit 12 advances the processing to step S18. On the other hand, when determining that the sleepiness level is lower than the predetermined threshold (the sleepiness is not generated) in step S17, the control unit 12 advances the processing to step S19.

In step S18, the control unit 12 operates as the awakening controller 12m, and performs the processing of outputting the predetermined control signal for awakening the driver 3 to the awakening device 70. When the awakening control is performed on the driver 3, the control unit 12 advances the processing to step S19. In the case where at least two threshold values are provided as the predetermined threshold in step S17, an awakening control signal corresponding to each threshold may be outputted. For example, a control signal for attracting attention by voice or the like may be output in the case where the sleepiness level is greater than or equal to the sleepiness sign stage and is less than the initial stage of the sleepiness, and a control signal for issuing an alarm by vibration or the like may be output in the case where the sleepiness level is greater than or equal to the initial stage of the sleepiness (doze state).

In step S19, the control unit 12 determines whether the starting switch 40 is turned off. When determining that the starting switch 40 is not turned off, the control unit 12 returns to the processing in step S1. On the other hand, when determining that the starting switch 40 is turned off in step S19, the control unit 12 advances the processing to step S20. In step S20, the control unit 12 stops the monitoring operation, and ends the processing.

[Operation and Effect]

In the data processing device 10 of one or more embodiments, the suitability degree evaluator 12d evaluates the suitability degree of the situation in calculating the vestibulo-ocular reflex movement, and the provision unit 12e provides the suitability degree (for example, the binary data indicating the presence or absence of the suitability or the multi-valued data indicating the rate of suitability) to the calculated data. Thus, what kind of the suitability is owned by the calculated data as the state of calculating the vestibulo-ocular reflex movement can be discriminated by the suitability degree provided to the calculated data.

The selector 12f selects the first technique of calculating the sleepiness based on the vestibulo-ocular reflex movement or the second technique of calculating the sleepiness based on the saccadic movement or the index relating to the eyelid movement, and the sleepiness is calculated based on the selected technique. For example, in the case where the data to which the suitability degree greater than or equal to the first threshold is provided among the pieces of calculated data stored for the predetermined time is greater than or equal to a predetermined proportion (for example, 80%), the first technique is selected, and the sleepiness is calculated based on the vestibulo-ocular reflex movement.

On the other hand, in the case where the data to which the suitability degree greater than or equal to the first threshold is provided among the pieces of calculated data stored for the predetermined time is less than the predetermined proportion (for example, 80%) (that is, the case is not suitable as the situation in which the VOR is calculated), the sleepiness is calculated by the second technique. Consequently, even in the situation that is not suitable for calculating the sleepiness by the first technique, namely, even in the situation that is not suitable for calculating the sleepiness based on the vestibulo-ocular reflex movement (for example, the situation with many noise components), the sleepiness can be calculated based on the second technique, and the sleepiness can stably be calculated with high accuracy in the real environment.

In the data processing device 10, the first sleepiness calculator 12g calculates the vestibulo-ocular reflex movement of the driver 3 based on the calculated data in consideration of the suitability degree, and calculates the sleepiness based on the calculated vestibulo-ocular reflex movement. Consequently, using the proper data in which the suitability degree is considered among the pieces of calculated data, the calculation accuracy of the vestibulo-ocular reflex movement can be enhanced, the sleepiness can accurately be calculated based on the vestibulo-ocular reflex movement, and the sign of the sleepiness can also be accurately evaluated in the real environment.

In the data processing device 10, the second sleepiness calculator 12i calculates the saccadic movement, and the sleepiness is calculated based on the calculated saccadic movement. This enables the sleepiness to be accurately calculated based on the saccadic movement in the situation that is not suitable for calculating the vestibulo-ocular reflex movement. In the data processing device 10, the second sleepiness calculator 12i calculates the index based on the eyelid movement such as the PERCLOS, and calculates the sleepiness based on the index based on the calculated eyelid movement. This enables the sleepiness to be accurately calculated based on the index based on the eyelid movement in the situation that is not suitable for calculating the vestibulo-ocular reflex movement.

The VOR calculator 12h of the data processing device 10 calculates the vestibulo-ocular reflex movement of the driver 3 using the calculated data to which the suitability degree higher than the second threshold is provided among the pieces of calculated data for t seconds stored in the calculated data storage 133. Thus, by narrowing down the calculated data used in the VOR calculation to the data having the high suitability, a calculation amount relating to the VOR calculation can be reduced, and the vestibulo-ocular reflex movement of the driver 3 can efficiently and accurately be calculated.

The data processing device 10 includes the first sleepiness calculator 12g and the second sleepiness calculator 12i, so that the sleepiness level of the driver 3 in the actual vehicle environment can accurately be calculated. The data processing device 10 includes the awakening controller 12m, so that the control of properly awakening the driver 3 can be performed according to the sleepiness level.

In the monitoring system 1 including the data processing device 10 and the camera 20, a driver monitoring system that is easily introduced in an actual vehicle environment can be provided. The awakening system including the data processing device 10 and the awakening device 70 can provide a system capable of properly awakening the driver 3 in the actual vehicle environment.

Other Embodiments

Although one or more embodiments are described in detail above, the above description is merely an example of the present invention in all respects. Various improvements and modifications can be made without departing from the scope of the present invention.

(First Modification)

The control unit 12 of the data processing device 10 does not need to include all the units in FIG. 3. In one or more embodiments, the control unit 12 may be constructed with a first configuration including at least the calculator 12c, the suitability degree evaluator 12d, the provision unit 12e, the selector 12f, the first sleepiness calculator 12g, and the second sleepiness calculator 12i or a second configuration further including an awakening controller 12m in addition to the first configuration.

Although the second sleepiness calculator 12i includes the saccadic movement calculator 12j and the eyelid movement calculator 12k, the second sleepiness calculator 12i may include one of the saccadic movement calculator 12j and the eyelid movement calculator 12k. The control unit 12 may include another eye movement calculator that is effective in calculating the sleepiness.

(Second Modification)

In the sleepiness calculation processing operation performed by the control unit 12 in FIG. 4B, whether the proportion of the calculated data to which the suitability degree higher than the first threshold is provided among the pieces of calculated data for t seconds is greater than or equal to n % may be determined in step S9. The suitability degree is not limited to the multi-valued data indicating the extent of suitability, but may be the binary data indicating the presence or absence of the suitability or the level of the suitability. In the case where the suitability degree is the binary data, whether the proportion of the calculated data to which the suitability degree indicating that the data is suitable or highly suitable is provided among the pieces of calculated data for t seconds is greater than or equal to n % may be determined in step S9.

(Third Modification)

In the sleepiness calculation processing performed by the control unit 12 in FIG. 4B, in step S10, the VOR of the driver 3 is calculated using the calculated data to which the suitability degree higher than the second threshold is provided among the pieces of calculated data for t seconds stored in the calculated data storage 133.

In one or more embodiments, in step S10, the VOR of the driver 3 may be calculated using the pieces of calculated data for the predetermined number of frames in descending order of the suitability degree among the pieces of calculated data for t seconds stored in the calculated data storage 133. With this configuration, by narrowing down the calculated data used in the VOR calculation to the data having the high suitability, the calculation amount relating to the VOR calculation can be reduced, and the VOR of the driver 3 can efficiently and accurately be calculated.

(Fourth Modification)

In one or more embodiments, the monitoring system 1 and the data processing device 10 are mounted on the vehicle 2. However, the monitoring system 1 and the data processing device 10 are not limited to in-vehicle use.

In one or more embodiments, for example, the monitoring system 1 and the data processing device 10 can be installed in a factory or in an office, and widely applied to a system that monitors the sleepiness of a person who operates equipment installed in the factory or a person who performs predetermined work at the desk. In this case, for example, a production device is operated by the person in the factory. For example, an office instrument such as a personal computer is operated by the person in the office.

[Supplementary Notes]

One or more embodiments may also be described as follows, but not limited thereto.

(Supplementary Note 1)

A data processing device (10) that performs data processing of monitoring a person, the data processing device (10) including:

a calculator (12c) configured to calculate pupil movement and head movement of the person;

an evaluator (12d) configured to evaluate a suitability degree of a situation in calculating vestibulo-ocular reflex movement based on the pupil movement and the head movement of the person;

a provision unit (12e) configured to provide the suitability degree evaluated by the evaluator (12d) to data relating to the pupil movement and the head movement of the person calculated by the calculator (12c);

a selector (12f) configured to select a first technique of calculating sleepiness based on the vestibulo-ocular reflex movement of the person or a second technique different from the first technique based on the suitability degree provided to the data;

a first sleepiness calculator (12g) configured to calculate the sleepiness based on the first technique when the selector (12f) selects the first technique; and a second sleepiness calculator (12i) configured to calculate the sleepiness based on the second technique when the selector (12f) selects the second technique.

(Supplementary Note 2)

A monitoring system (1) including:

the data processing device (10); and an imaging device (20) configured to capture an image including the person, wherein the calculator (12c) of the data processing device (10) calculates the pupil movement and the head movement of the person using the image acquired from the imaging device (20).

(Supplementary Note 3)

A data processing method for monitoring a person, the data processing method including:

a calculation step (S3, S4) of calculating pupil movement and head movement of the person;

an evaluation step (S5) of evaluating a suitability degree of a situation in calculating vestibulo-ocular reflex movement based on the pupil movement and the head movement of the person;

a provision step (S6) of providing the suitability degree evaluated in the evaluation step (S5) to data relating to the pupil movement and the head movement of the person calculated in the calculation step (S3, S4);

a selection step (S9) of selecting a first technique of calculating sleepiness based on the vestibulo-ocular reflex movement of the person or a second technique different from the first technique based on the suitability degree provided to the data;

a first sleepiness calculation step (S10, S11) of calculating the sleepiness based on the first technique when the first technique is selected in the selection step (S9); and a second sleepiness calculation step (S10, S11) of calculating the sleepiness based on the second technique when the second technique is selected in the selection step (S9).

(Supplementary Note 4)

A data processing program causing at least one computer (12) to perform data processing of monitoring a person, the data processing program causing the at least one computer (12) to perform:

a calculation step (S3, S4) of calculating pupil movement and head movement of the person;

an evaluation step (S5) of evaluating a suitability degree of a situation in calculating vestibulo-ocular reflex movement based on the pupil movement and the head movement of the person;

a provision step (S6) of providing the suitability degree evaluated in the evaluation step (S5) to data relating to the pupil movement and the head movement of the person calculated in the calculation step (S3, S4);

a selection step (S9) of selecting a first technique of calculating sleepiness based on the vestibulo-ocular reflex movement of the person or a second technique different from the first technique based on the suitability degree provided to the data;

a first sleepiness calculation step (S10, S11) of calculating the sleepiness based on the first technique when the first technique is selected in the selection step (S9); and a second sleepiness calculation step (S12 to S16) of calculating the sleepiness based on the second technique when the second technique is selected in the selection step.

The invention claimed is:

1. A data processing device that performs data processing of monitoring a person, the data processing device comprising a processor configured with a program to perform operations comprising:

operation as a calculator configured to calculate pupil movement and head movement of the person;

operation as an evaluator configured to evaluate a suitability degree of a situation in calculating vestibulo-ocular reflex movement based on the pupil movement and the head movement of the person;

operation as a provision unit configured to provide the suitability degree evaluated by the evaluator to data relating to the pupil movement and the head movement of the person calculated by the calculator;

operation as a selector configured to select a first technique of calculating sleepiness based on the vestibulo-ocular reflex movement of the person or a second technique different from the first technique based on the suitability degree provided to the data;

operation as a first sleepiness calculator configured to calculate the sleepiness based on the first technique when the selector selects the first technique; and operation as a second sleepiness calculator configured to calculate the sleepiness based on the second technique when the selector selects the second technique.

2. The data processing device according to claim 1, wherein the processor is configured with the program to perform operations such that:

operation as the selector is further configured to select the first technique when the suitability degree satisfies a predetermined condition; and operation as the selector is further configured to select the second technique when the suitability degree does not satisfy the predetermined condition.

3. The data processing device according to claim 2, wherein the processor is configured with the program to perform operations such that operation as the first sleepiness calculator comprising operation as a reflex movement calculator configured to calculate the vestibulo-ocular reflex movement of the person based on the data in consideration of the suitability degree, and the sleepiness is calculated based on the vestibulo-ocular reflex movement of the person calculated by the reflex movement calculator.

4. The data processing device according to claim 2, wherein the processor is configured with the program to perform operations such that operation as the second sleepiness calculator comprising operation as a saccadic movement calculator configured to calculate saccadic movement of an eye of the person, and the sleepiness is calculated based on the saccadic movement of the person calculated by the saccadic movement calculator.

5. The data processing device according to claim 2, wherein the processor is configured with the program to perform operations such that operation as the second sleepiness calculator comprising operation as an eyelid movement calculator configured to calculate an index based on eyelid movement of the person, and the sleepiness is calculated based on the index based on the eyelid movement calculated by the eyelid movement calculator.

6. The data processing device according to claim 2, wherein the processor is configured with the program to perform operations further comprising operation as an awakening controller configured to perform control of awakening the person based on the sleepiness calculated by the first sleepiness calculator or the second sleepiness calculator.

7. The data processing device according to claim 2, wherein the processor is configured with the program to perform operations such that operation as the evaluator is further configured to evaluate the suitability degree based on a state of the person or an object operated by the person.

8. The data processing device according to claim 7, wherein the object comprises a vehicle, and the person comprises a driver of the vehicle.

9. The data processing device according to claim 1, wherein the processor is configured with the program to perform operations such that operation as the first sleepiness calculator comprising operation as a reflex movement calculator configured to calculate the vestibulo-ocular reflex movement of the person based on the data in consideration of the suitability degree, and the sleepiness is calculated based on the vestibulo-ocular reflex movement of the person calculated by the reflex movement calculator.

10. The data processing device according to claim 1, wherein the processor is configured with the program to perform operations such that operation as the second sleepiness calculator comprising operation as a saccadic movement calculator configured to calculate saccadic movement of an eye of the person, and the sleepiness is calculated based on the saccadic movement of the person calculated by the saccadic movement calculator.

11. The data processing device according to claim 1, wherein the processor is configured with the program to perform operations such that operation as the second sleepiness calculator comprising operation as an eyelid movement calculator configured to calculate an index based on eyelid movement of the person, and the sleepiness is calculated based on the index based on the eyelid movement calculated by the eyelid movement calculator.

12. The data processing device according to claim 1, wherein the processor is configured with the program to perform operations further comprising operation as an awakening controller configured to perform control of awakening the person based on the sleepiness calculated by the first sleepiness calculator or the second sleepiness calculator.

13. An awakening system comprising:

the data processing device according to claim 12; and an awakening device controlled by the awakening controller of the data processing device.

14. The data processing device according to claim 1, wherein the processor is configured with the program to perform operations such that operation as the evaluator is further configured to evaluate the suitability degree based on a state of the person or an object operated by the person.

15. The data processing device according to claim 14, wherein
the object comprises a vehicle, and
the person comprises a driver of the vehicle.

16. The data processing device according to claim 15, wherein the processor is configured with the program to perform operations such that operation as the evaluator is further configured to evaluate the suitability degree based on at least one of a noise component included in the data, a sight line direction of the driver, a running state of the vehicle, and a detection state of the object existing in a traveling direction of the vehicle.

17. The data processing device according to claim 15, wherein
the processor is configured with the program to perform operations further comprising operation as an acquisition unit configured to acquire acceleration of the vehicle, and
the processor is configured with the program to perform operations such that operation as the evaluator is further configured to evaluate the suitability degree based on a relationship between a change in acceleration of the vehicle acquired from the vehicle and the head movement or the pupil movement of the driver calculated by the calculator.

18. A monitoring system comprising:
the data processing device according to claim 1; and
an imaging device configured to capture an image including the person, wherein the calculator of the data processing device calculates the pupil movement and the head movement of the person using the image acquired from the imaging device.

19. A data processing method for monitoring a person, the data processing method comprising:
calculating pupil movement and head movement of the person;
evaluating a suitability degree of a situation in calculating vestibulo-ocular reflex movement based on the pupil movement and the head movement of the person;
providing the evaluated suitability degree to data relating to the calculated pupil movement and the calculated head movement of the person;
selecting a first technique of calculating sleepiness based on the vestibulo-ocular reflex movement of the person or a second technique different from the first technique based on the suitability degree provided to the data;
calculating the sleepiness based on the first technique in response to selecting the first technique; and
calculating the sleepiness based on the second technique in response to selecting the second technique.

20. A non-transitory computer-readable storage medium storing a data processing program, which when read and executed, causes at least one computer to perform data processing of monitoring a person, the data processing program, which when read and executed, causes the at least one computer to perform operations comprising:
calculating pupil movement and head movement of the person;
evaluating a suitability degree of a situation in calculating vestibulo-ocular reflex movement based on the pupil movement and the head movement of the person;
providing the evaluated suitability degree to data relating to the calculated pupil movement and the calculated head movement of the person;
selecting a first technique of calculating sleepiness based on the vestibulo-ocular reflex movement of the person or a second technique different from the first technique based on the suitability degree provided to the data;
calculating the sleepiness based on the first technique in response to selecting the first technique; and
calculating the sleepiness based on the second technique in response to selecting the second technique.

* * * * *